United States Patent
Honguh et al.

(10) Patent No.: US 8,131,192 B2
(45) Date of Patent: Mar. 6, 2012

(54) IMAGE FORMING APPARATUS FOR FORMING IMAGE ON RECORD MEDIUM

(75) Inventors: Yoshinori Honguh, Yokohama (JP); Takeshi Morino, Edogawa-ku (JP)

(73) Assignees: Kabushiki Kaisha Toshiba, Tokyo (JP); Toshiba Tec Kabushiki Kaisha, Tokyo (JP)

( * ) Notice: Subject to any disclaimer, the term of this patent is extended or adjusted under 35 U.S.C. 154(b) by 1359 days.

(21) Appl. No.: 11/735,715

(22) Filed: Apr. 16, 2007

(65) Prior Publication Data

US 2008/0252909 A1 Oct. 16, 2008

(51) Int. Cl.
G03G 15/00 (2006.01)
G03G 21/00 (2006.01)
B65H 7/14 (2006.01)

(52) U.S. Cl. .................................. 399/289; 399/45

(58) Field of Classification Search .................... 399/45, 399/389
See application file for complete search history.

(56) References Cited

U.S. PATENT DOCUMENTS

| | | | | |
|---|---|---|---|---|
| 5,689,757 A | * | 11/1997 | Ferrante et al. | 399/45 |
| 5,713,063 A | * | 1/1998 | Oono | 399/66 |
| 7,193,642 B2 | * | 3/2007 | Hirai et al. | 347/236 |
| 2008/0253782 A1 | * | 10/2008 | Honguh | 399/45 |

FOREIGN PATENT DOCUMENTS

| | | | | |
|---|---|---|---|---|
| JP | 02056375 A | * | 2/1990 |
| JP | 06015861 A | * | 1/1994 |
| JP | 06040605 A | * | 2/1994 |
| JP | 06056313 A | * | 3/1994 |
| JP | 06100203 A | * | 4/1994 |
| JP | 07097099 A | * | 4/1995 |
| JP | 10039556 A | * | 2/1998 |
| JP | 10198174 A | * | 7/1998 |
| JP | 11212405 A | * | 8/1999 |
| JP | 2000063004 A | * | 2/2000 |
| JP | 2000171416 A | * | 6/2000 |
| JP | 2000284551 A | * | 10/2000 |
| JP | 2003-212391 | | 7/2003 |
| JP | 2004109051 A | * | 4/2004 |
| JP | 2005-075469 | | 3/2005 |
| JP | 2005075469 A | * | 3/2005 |
| JP | 2005315856 A | * | 11/2005 |
| JP | 2007033069 A | * | 2/2007 |

OTHER PUBLICATIONS

Machine translation of JP 06056313 A, JPO, Feb. 17, 2011.*
Machine translation of JP 2005315856 A, JPO, Jul. 20, 2011.*

* cited by examiner

*Primary Examiner* — Matthew G Marini
*Assistant Examiner* — Nguyen Q Ha
(74) *Attorney, Agent, or Firm* — Turocy & Watson, LLP

(57) ABSTRACT

A record-medium determining apparatus constituted such that a luminescent light source irradiates modulated light to a surface of a record medium, a part of reflected light by the record medium of this irradiated light is detected by a photodetector, the photodetector changes the detected light into an electric signal, and a signal-intensity detecting device detects intensity of a signal modulated from this electric signal is provided further on an upstream side than a fixing unit of a record-medium conveying path.

11 Claims, 16 Drawing Sheets

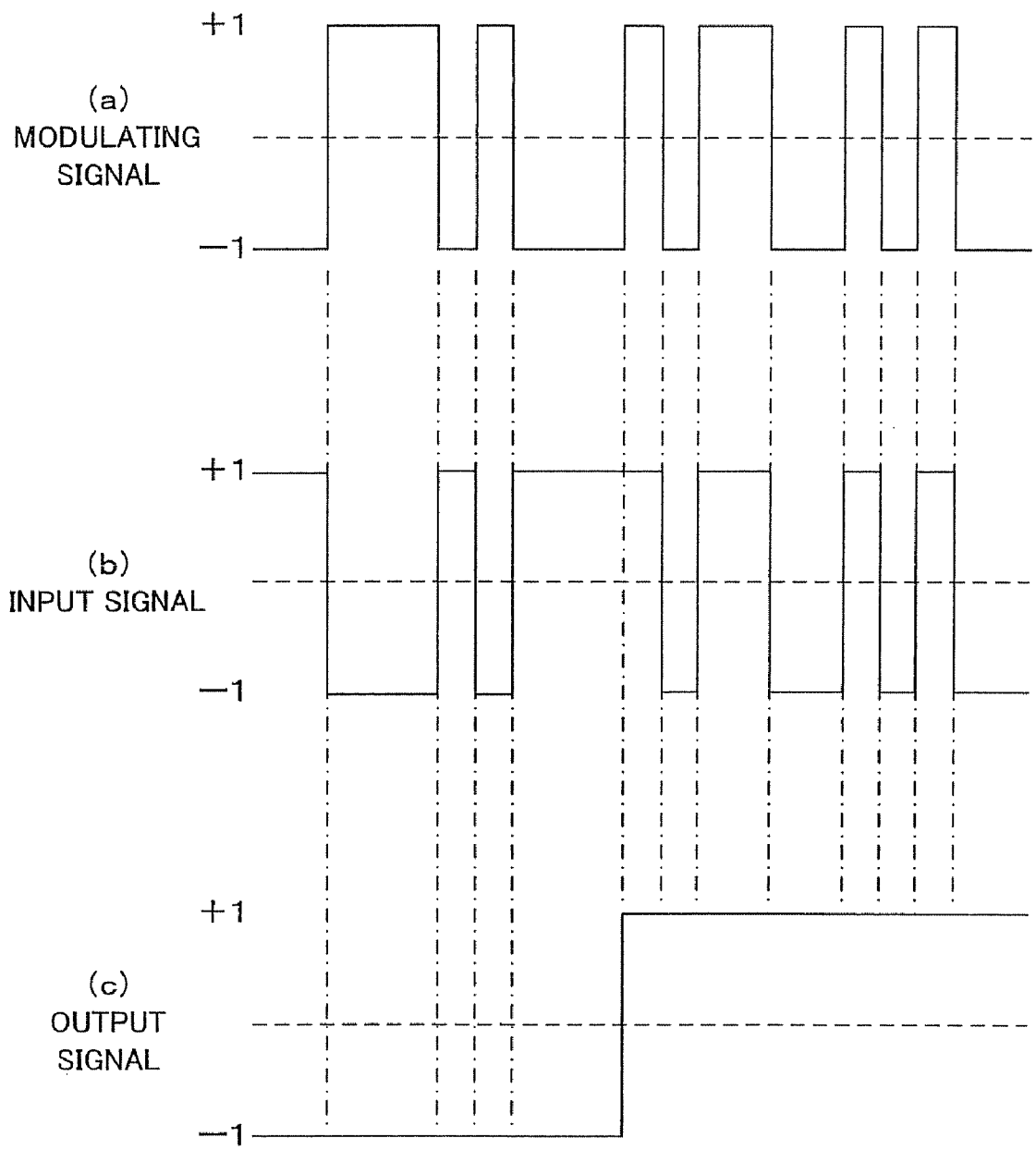

MODULATION PATTERN
(LUMINESCENT LIGHT SOURCE)

MODULATION PATTERN
(LUMINESCENT LIGHT SOURCE)

MODULATION PATTERN
(LUMINESCENT LIGHT SOURCE)

IMAGE FORMING APPARATUS FOR FORMING IMAGE ON RECORD MEDIUM

BACKGROUND OF THE INVENTION

1. Field of the Invention

The present invention relates to an image forming apparatus that forms an image on a record medium, the image forming apparatus including a record-medium determining apparatus that determines a type of the record medium by irradiating modulated light on the record medium and detecting intensity of reflected light of the light.

2. Description of the Related Art

In order to perform high-quality image formation in image forming apparatuses such as a copying machine and a printer, it is necessary to adjust a printing method to a type of a record medium such as a sheet on which an image is formed. For example, when an image is printed on plain paper and when an image is printed on an OHP sheet, a high-quality image is not obtained unless the printing method is adjusted to the plain paper and the OHP sheet.

An operator manually selected a type of a record medium in models at the initial stage. However, since the operator sometimes makes mistakes in the selection, apparatuses that detect types of sheets have been developed.

In the conventional technique, an apparatus is proposed which reflects light of one LED light source on a sheet and detects reflected light of the light with optical sensors provided in a regular reflection direction and a diffuse reflection direction. (E.g., JP-A-2005-75469).

This apparatus determines a type of a sheet by changing a quantity of light of the LED light source and comparing the reflected light detected by the respective optical sensors with a threshold set in advance.

However, in this technique, there is a problem in that, when light other than the light of the LED light source is present, since this light is made incident on the optical sensors as noise, it is impossible to determine a type of the sheet.

Moreover, the technique has a problem in that it is necessary to lead a sheet set as a reference into the image forming apparatus and perform calibration in order to compare the reflected light with the threshold, resulting in a burden on an operator.

BRIEF SUMMARY OF THE INVENTION

It is an object of the present invention to provide an image forming apparatus that forms an image on a record medium, the imaging forming apparatus including a record-medium determining apparatus that determines a type of the record medium by irradiating modulated light on the record medium and detecting intensity of reflected light of the light.

In an aspect of the present invention, an image forming apparatus that forms an image on a record medium includes:

a luminescent light source that irradiates light to a surface of the record medium;

a driving device that gives modulation to the irradiated light irradiated from the luminescent light source;

a photodetector that detects reflected light irradiated from the luminescent light source and reflected by the record medium;

a light shielding plate that has a through hole provided such that, when the irradiated light totally reflects on the surface of the record medium, reflected light of the irradiated light irradiated from a specific portion of the luminescent light source is made incident on the photodetector and reflected light of the irradiated light irradiated from other portions of the luminescent light source is not made incident on the photodetector; and a signal-intensity detecting device that determines a type of the record medium by detecting intensity of a signal modulated from an output signal outputted by converting the light detected by the photodetector.

DESCRIPTION OF THE DRAWINGS

FIG. 8 is a diagram showing a modulating signal, an input signal from an A/D converter, and an integration result;

DETAILED DESCRIPTION OF THE INVENTION

Throughout this description, the embodiments and examples shown should be considered as exemplars, rather than limitations on the apparatus and methods of the present invention.

An embodiment of an image forming apparatus that forms an image on a record medium according to the present invention will be explained in detail using the drawings.

<Record-Medium Determining Apparatus>

First, a record-medium determining apparatus will be explained.

First Embodiment

A schematic structure of a record-medium determining apparatus according to a first embodiment will be explained. This embodiment is characterized in that plural luminescent light sources are provided in the record-medium determining apparatus, different modulations are given to each of the luminescent light sources, and a type of a record medium is determined by extracting a signal synchronizing with a modulating signal.

Figure 1:
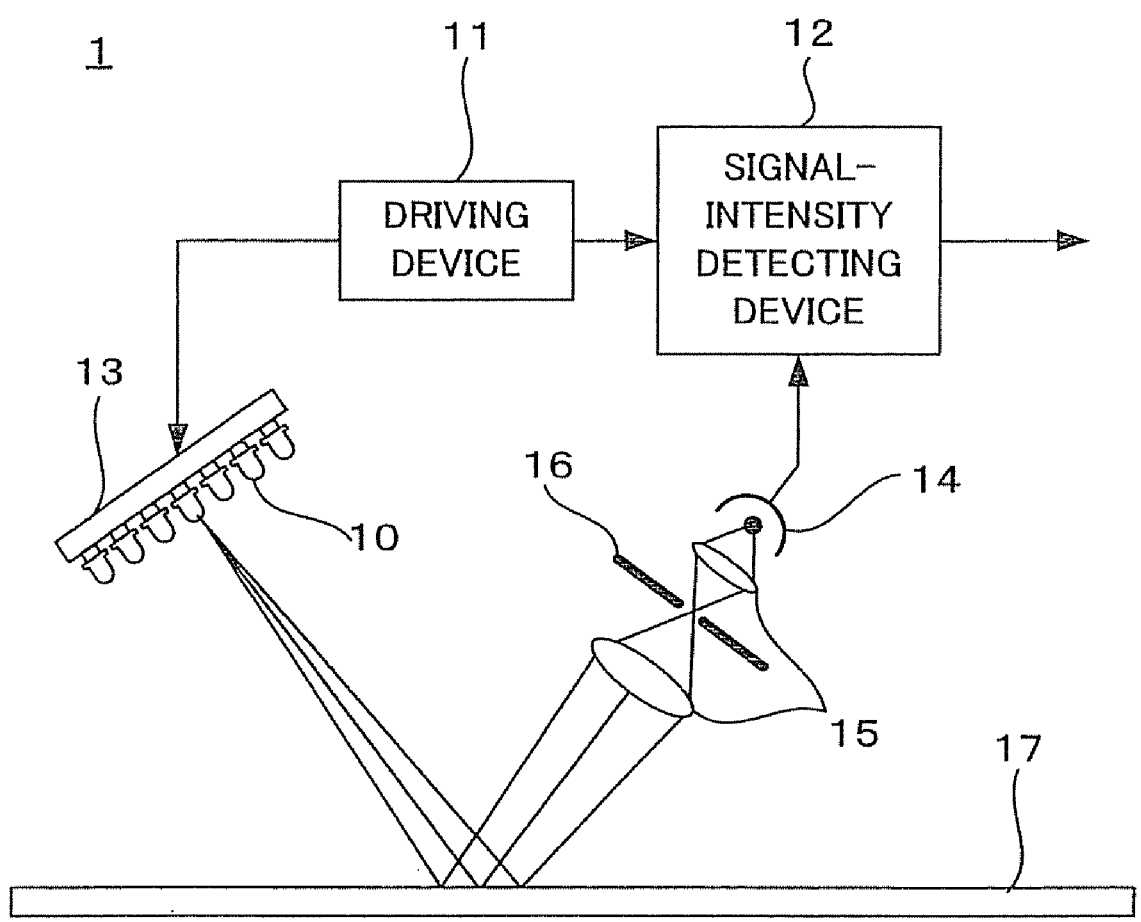
FIG. 1 is a diagram schematically showing a record-medium determining apparatus according to a first embodiment.

FIG. 1 is a diagram schematically showing the record-medium determining apparatus according to this embodiment. A record-medium determining apparatus 1 according to this embodiment includes a light emitting device 13 including plural luminescent light sources 10 that irradiate light to a surface of a record medium, a driving device 11 that gives different modulations to each of the luminescent light sources 10, a light shielding plate 16 that has a through hole, a photodetector 14 that detects irradiated light reflected on a surface of a record medium 17, and a signal-intensity detecting device 12 that determines a type of the record medium by detecting intensity of a signal from an output signal outputted by converting light detected by the photodetector 14.

The luminescent light sources 10 only have to be light sources that can modulate irradiated light. It is possible to use, for example, LEDs. In this embodiment, the luminescent light sources 10 will be explained using seven luminescent light sources 10 arranged in a row in the light-emitting device 13 as an example.

The photodetector 14 only has to have a function of converting light into an electric signal. It is possible to select a type of the photodetector 14 as appropriate. The photodetector may be constituted to condense light with lenses 15.

Figure 2:
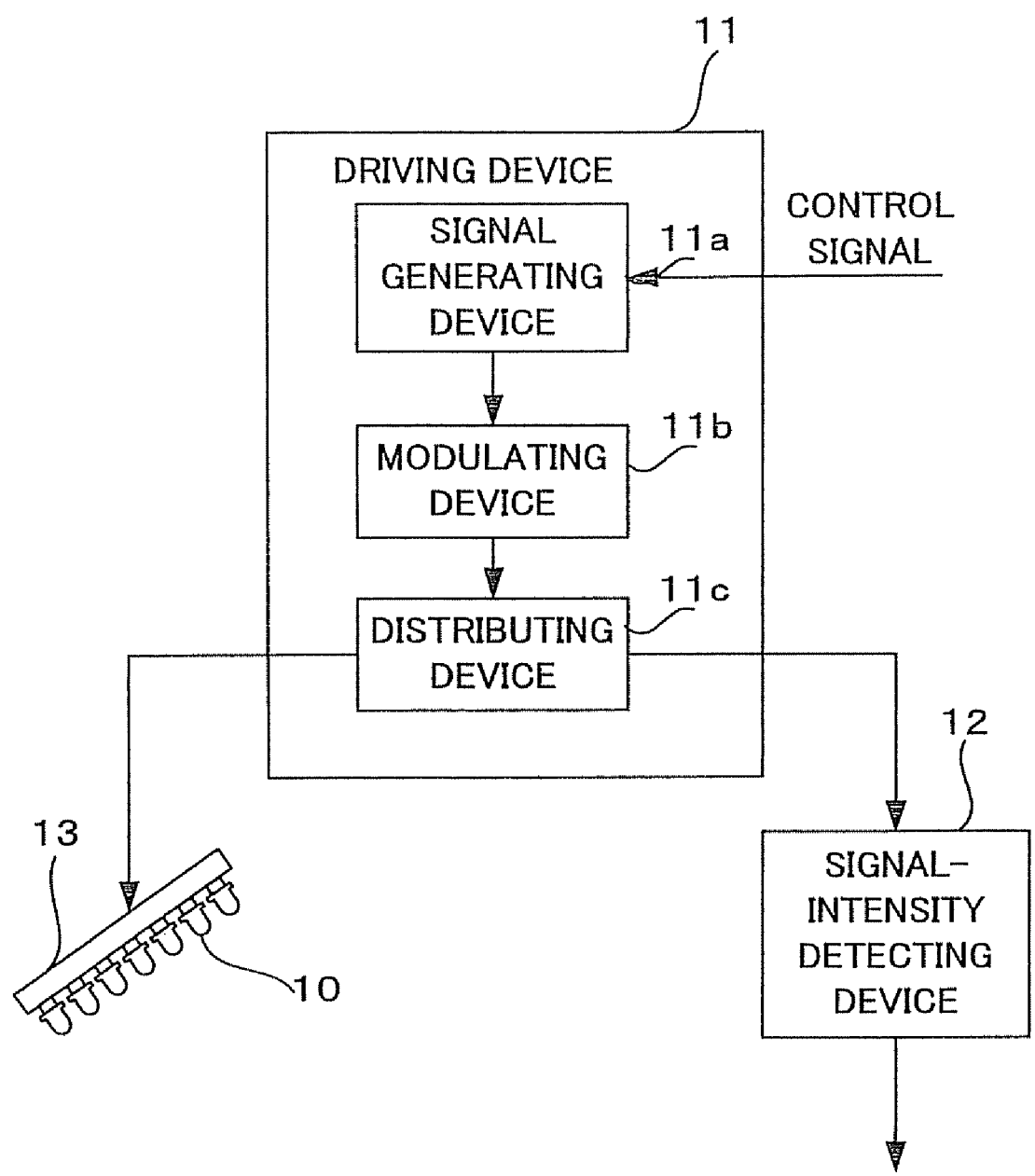
FIG. 2 is a diagram showing an example of a structure of a driving device.

FIG. 2 is a diagram showing an example of a structure of the driving device 11. The driving device value 11 includes a signal generating device 11a that is inputted with a control signal from an external apparatus and generates a signal, a modulating device 11b that is inputted with the signal from the signal generating device 11a and generates a modulating signal for giving different modulations to each of the luminescent light sources 10, and a distributing device 11c that distributes the modulating signal inputted from the modulating device 11b to the respective luminescent light sources 10 and the signal-intensity detecting device 12.

Light-emitting elements such as LEDs that irradiate light of different wavelengths may be used in the luminescent light sources 10 without providing the driving device 11.

Figure 3A:
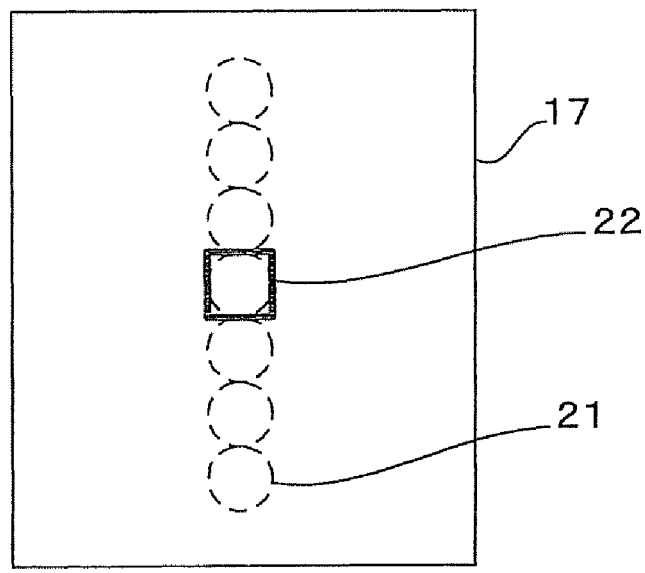
FIG. 3A is a diagram representing reflected light at the time when a record medium totally reflects irradiated light.
Figure 3B:
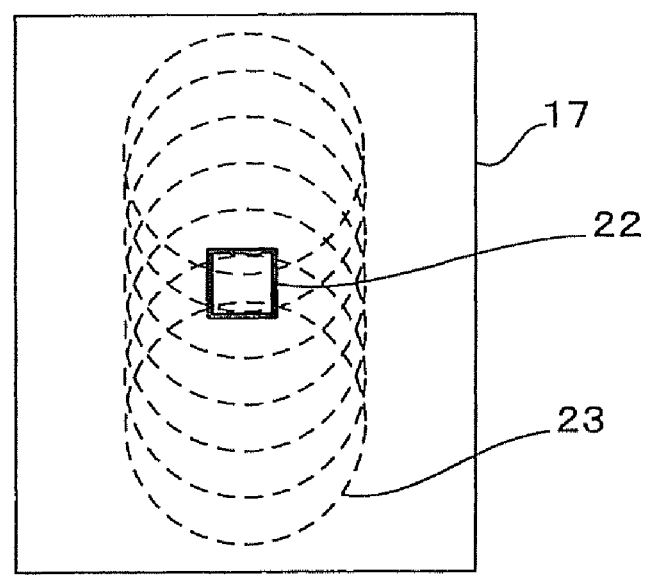
FIG. 3B is a diagram representing reflected light on a record medium having a little gloss on a surface thereof.

FIG. 3A and FIG. 3B are diagrams representing reflected light on record media having different glossiness.

FIG. 3A is a diagram representing reflected light at the time when the record medium 17 totally reflects irradiated light. Irradiated lights 21 reflect on the surface of the record medium 17 side by side without practically overlapping one another.

In this case, the through hole of the light shielding plate 16 is provided such that reflected light reflected by the record medium 17 of the irradiated light irradiated from a specific luminescent light source 10 is made incident on the photodetector 14 and other reflected lights are not made incident on the photodetector 14. When the through hole is provided in this way, the reflected light made incident on the photodetector 14 is as indicated by a field of view 22.

A position in the light shielding plate 16 and a size of the through hole of the light shielding plate 16 depend on a size and a distance from the record medium 17 of the luminescent light sources 10, focal lengths and positions of the lenses 15, a position of the light shielding plate 16, and the like.

"The other reflected lights are not made incident" does not means that the other reflected lights are not made incident at all and does not require that the other reflected lights are not made incident at all. It is inevitable that the other reflected lights are slightly made incident. Even in this case, according to this embodiment, it is possible to determine a type of the record medium 17.

The through hole is a fractured section that is provided in the light shielding plate 16 and causes light to pass. This through hole may be a mere hole or may be formed of a transparent material such as glass. A shape of the through hole is not limited to a rectangle.

FIG. 3B is a diagram representing reflected light on the record medium 17 having a little gloss on the surface thereof. The irradiated lights 21 are irradiated on the surface of the record medium 17 overlapping one another. Reflected light from the plural luminescent light sources 10 is made incident on the field of view 22.

In this way, the number of irradiated lights of the luminescent light sources 10 made incident on the photodetector 14, i.e., a type of a modulating signal is different depending on a type of the record medium 17. Thus, modulations different for each of the light-emitting sources 10 are given to the irradiated lights of the respective luminescent light sources 10 and a signal synchronizing with the modulating signal is extracted from reflected light made incident on the photodetector 14.

As types of modulating signals extracted are fewer, a record medium reflects light better. As types of modulating signals extracted are more, a record medium diffuses light more. The signal-intensity detecting device 12 detects, using this fact, glossiness of a record medium according to whether the number of modulating signals extracted is large or small and determines a type of the record medium according to the glossiness.

An example in which a frequency of irradiated light is changed (a first applied example) and an example in which a blinking pattern of irradiated light is changed (a second applied example) will be hereinafter explained as examples of a modulation form.

(First Applied Example)

The driving device 11 outputs a modulating signal for the respective luminescent light sources 10 to emit light at different frequencies to the light emitting device 13.

Figure 4:
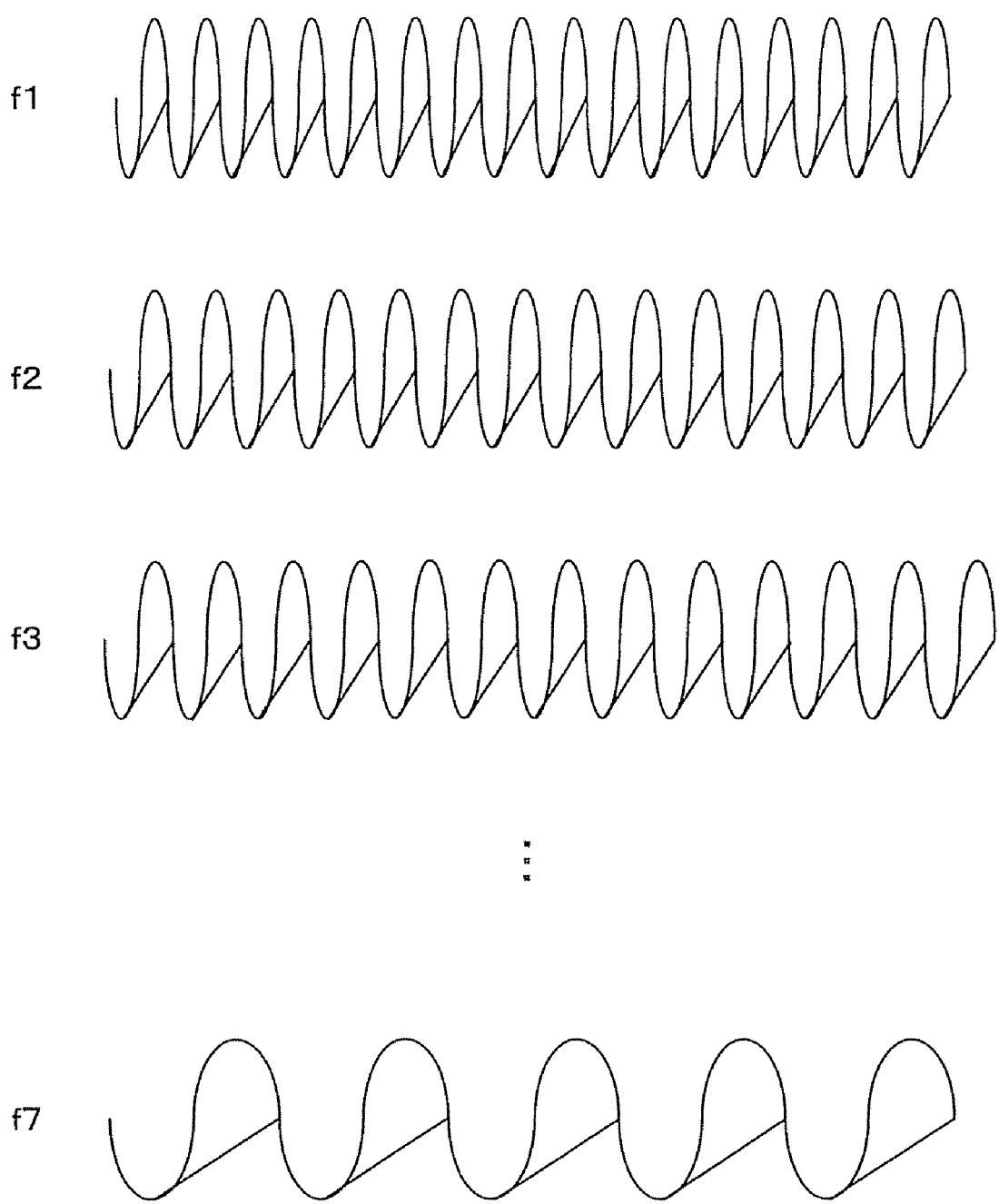
FIG. 4 is a diagram schematically representing an example of a frequency modulated for each light-emitting source.

FIG. 4 is a diagram schematically representing an example of a frequency modulated for each of the luminescent light sources 10. f1 to f7 correspond to the respective luminescent light sources 10. In this way, for example, wave lengths of light irradiated from the respective luminescent light sources are increased in order.

Figure 5:
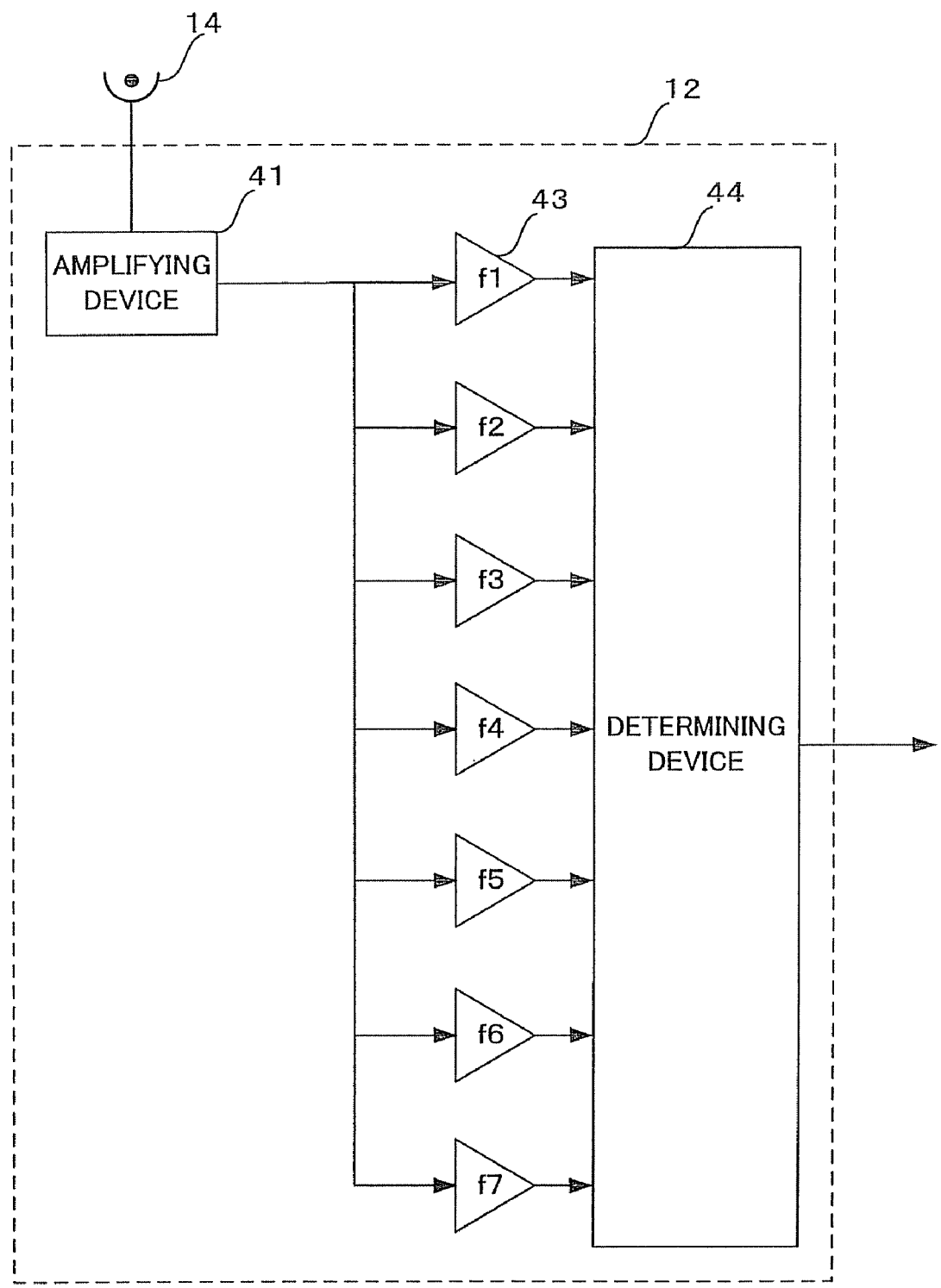
FIG. 5 is a schematic diagram showing a structure and a connection relation of a signal-intensity detecting device in a first applied example.

FIG. 5 is a schematic diagram showing a structure and a connection relation of the signal-intensity detecting device 12. Irradiated light reflected on the medium 17 is detected and converted into an electric signal by the photodetector 14. This converted output signal is inputted to the signal-intensity detecting device 12.

The signal-intensity detecting device 12 has an amplifying device 41 that amplifies a signal, band-pass filters 43 that cause each of frequencies modulated to pass and attenuate the other frequencies, and a determining device 44 that compares amplitudes of signals outputted from the respective band-pass filters 43.

It is also possible to provide the determining device 44 on the outside of the signal-intensity detecting device 12, for example, integrally with a control unit of the image forming apparatus. It is possible to constitute the determining device 44, for example, as described below. The determining device 44 includes an A/D converter that changes analog data to digital data, a processor such as a digital signal processor, and a memory that stores data. Moreover, the determining device 44 is inputted with digital data from the A/D converter, compares amplitudes at respective modulation frequencies, and stores a program describing processing for determining glossiness of the record medium 17 in the memory. The processor reads the program from this memory and executes the processing.

The output signal amplified by the amplifying device 41 is inputted to the respective band-pass filters 43. The respective band-pass filters 43 extract signals of modulated frequencies given to the respective luminescent light sources 10 from the output signal inputted. The extracted signals are inputted to the determining device 44.

Figure 6:
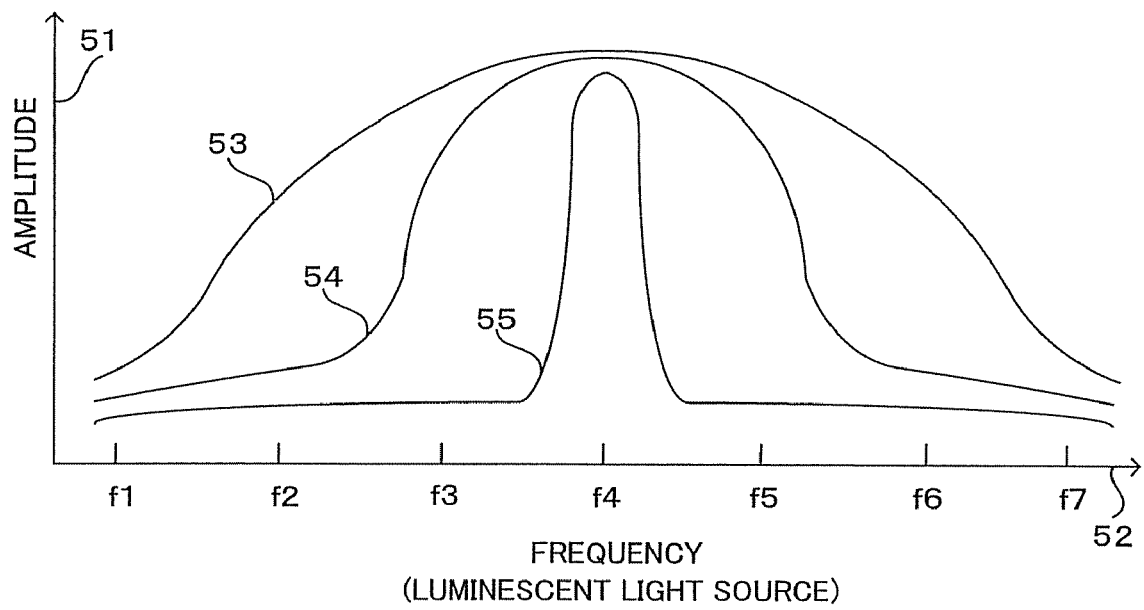
FIG. 6 is a graph in which amplitudes of extracted signals are plotted for each of modulated frequencies.

FIG. 6 is a graph in which amplitudes of the extracted signals are plotted for each of the modulated frequencies. An ordinate 51 indicates amplitude and an abscissa 52 indicates the respective frequencies modulated for each of the luminescent light sources 10.

When the record medium 17 is a record medium having a gloss on a surface thereof and reflects light irradiated from the luminescent light sources 10 well, light other than light from f4 among the luminescent light sources 10 is hardly made incident on the photodetector 14. Therefore, as indicated by a graph 55, amplitude of a frequency of the light irradiated from f4 is large and amplitudes of the other frequencies are small.

When the record medium 17 is a record medium having a little gloss on a surface thereof and reflects light irradiated from the luminescent light sources 10 to some extent, light from f3 and f5 other than f4 among the luminescent light sources 10 is also made incident on the photodetector 14. Therefore, as indicated by a graph 54, amplitude of a frequency of the light irradiated from f4 is large, amplitudes of frequencies of the light irradiated from f3 and f5 are slightly large, and amplitudes of the other frequencies are small.

When the record medium 17 is a record medium having little gloss on a surface thereof and does not reflect light irradiated from the luminescent light sources 10 well, light from f2 and f6 in addition to f4, f3, and f5 among the luminescent light sources 10 is also made incident on the photodetector 14. Therefore, as indicated by a graph 53, amplitude of a frequency of the light irradiated from f4 is large, amplitudes of frequencies of the light irradiated from f3 and f5 are slightly large, amplitudes of frequencies of the light irradiated from f2 and f6 are medium, and amplitudes of the other frequencies are small.

As described above, in this applied example, the determining device 44 detects amplitudes of respective frequencies modulated for each of the light-emitting sources 10 included in reflected light, determines glossiness on the surface of the record medium 17 according to the amplitudes, and determines a type of the record medium from this glossiness on the surface.

The determining device 44 determines that the record medium is, for example, an OHP film when the number of frequencies detected is one, high-quality plain paper when the number of frequencies detected is three, and plain paper when the number of frequencies detected is five.

(Second Applied Example)

The driving device 11 outputs a modulating signal for the respective luminescent light sources 10 to emit light in different blinking patterns to the respective luminescent light sources 10. Consequently, the respective luminescent light sources 10 blink in the different blinking patterns.

Figure 7:
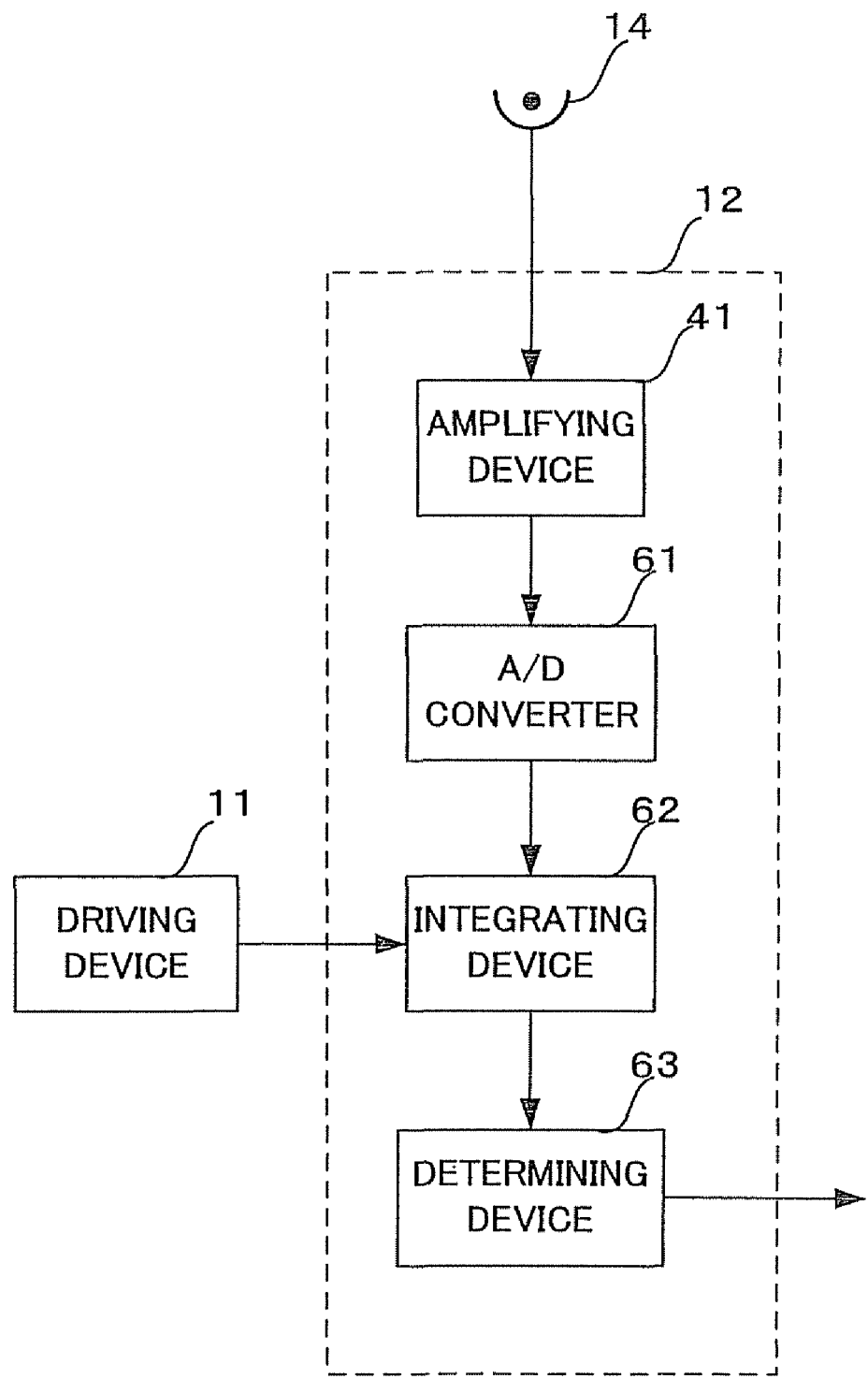
FIG. 7 is schematic diagram showing a structure and a connection relation of a signal-intensity detecting device in a second applied example.

FIG. 7 is a schematic diagram showing a structure and a connection relation of the signal-intensity detecting device 12. Irradiated light reflected on the medium 17 is detected and converted into an electric signal by the photodetector 14. This converted output signal is inputted to the signal-intensity detecting device 12.

The signal-intensity detecting device 12 has an amplifying device 41 that amplifies a signal, an A/D converter 61 that converts an analog signal into a digital signal, an integrating device 62 that integrates a signal inputted from the A/D converter 61 and a signal inputted from the driving device, and a determining device 63 that compares an integrated value, which is a value of the integration outputted from the integrating device 62.

It is also possible to provide this determining device 63 on the outside of the signal-intensity detecting device 12, for example, integrally with the image forming apparatus. It is also possible to constitute the integrating device 62 and the determining device 63 as an integral device.

It is possible to constitute the integrating device 62 and the determining device 63, for example, as described below. The integrating device 62 and the determining device 63 include processors such as digital signal processors and memories that store data. Moreover, the integrating device 62 is inputted with digital data from the A/D converter 61, integrates the digital data and a modulating signal inputted from the driving device 11 for each of modulated frequencies, and stores a program describing processing for determining glossiness of the record medium 17 from this integrated value in the memory. The processor reads the program from this memory and executes the processing.

FIG. 8 is a diagram showing an integration result of the modulating signal and the input signal from the A/D converter 61. Blinking patterns of the respective luminescent light sources 10 are different from one another. Here, extraction of light irradiated from one luminescent light source 10 will be explained.

FIG. 8(*a*) is a diagram showing an example of the modulating signal inputted from the driving 11 to the integrating device 62. This modulated irradiated light is irradiated on the record medium 17 and reflected. For example, irradiation of the light is represented as +1 and non-irradiation of the light is represented as −1.

FIG. 8(*b*) is a diagram showing an example in which irradiated light irradiated from the respective luminescent light sources 10 and reflected by the record medium 17 is detected and converted into an electric signal by the photodetector 14. A signal outputted from this photodetector 14 is inputted to the synchronizing signal intensity detecting device 12, amplified by the amplifying device 41, and, then, converted into digital data by the A/D converter 61. The A/D converter 61 sets, for example, detection of light as +1 and non-detection of light as −1. The signal converted into the digital data is inputted to the integrating device 62 of the synchronizing signal intensity detecting device 12.

The integrating device 62 outputs +1 when the modulating signal is +1 and the output signal is +1 and when the modulating signal is −1 and the output signal is −1, i.e., when the modulating signal and the output signal coincide with each other. Otherwise, the integrating device 62 outputs −1.

FIG. 8(c) is a diagram representing an integrated value outputted from the integrating device 62. As shown in the figure, the integrating device 62 sequentially extracts the light irradiated by the respective luminescent light sources 10 from the irradiated light reflected by the record medium 17.

In FIG. 8(b) and FIG. 8(c), logical patterns are shown for explanation. In actual measurement, when irradiated light from a certain luminescent light source 10 is not included, integrated values obtained by the integrating device 62 are averaged to 0. Therefore, it is possible to detect irradiated light from a specific luminescent light source 10 by calculating an average of integrated values.

Figure 9A:
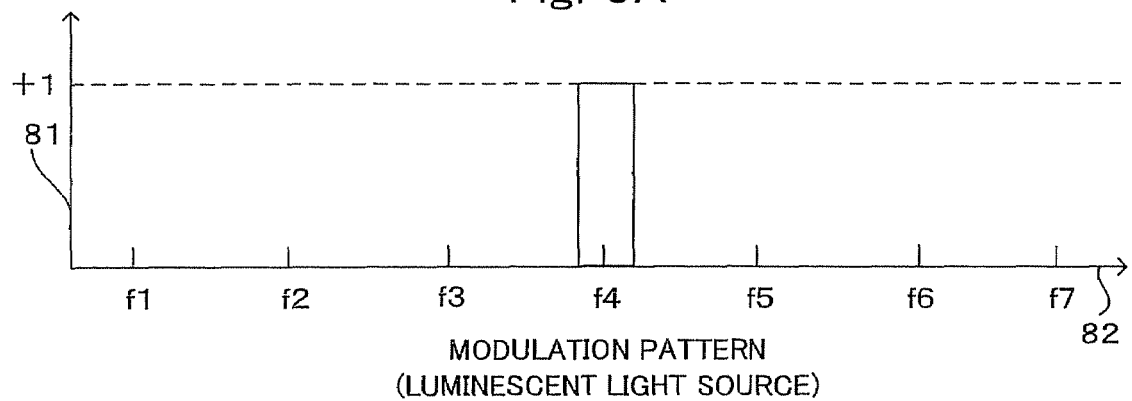
FIG. 9A is a diagram representing an integrated value for each modulation pattern on a record medium having a gloss on a surface thereof.
Figure 9B:
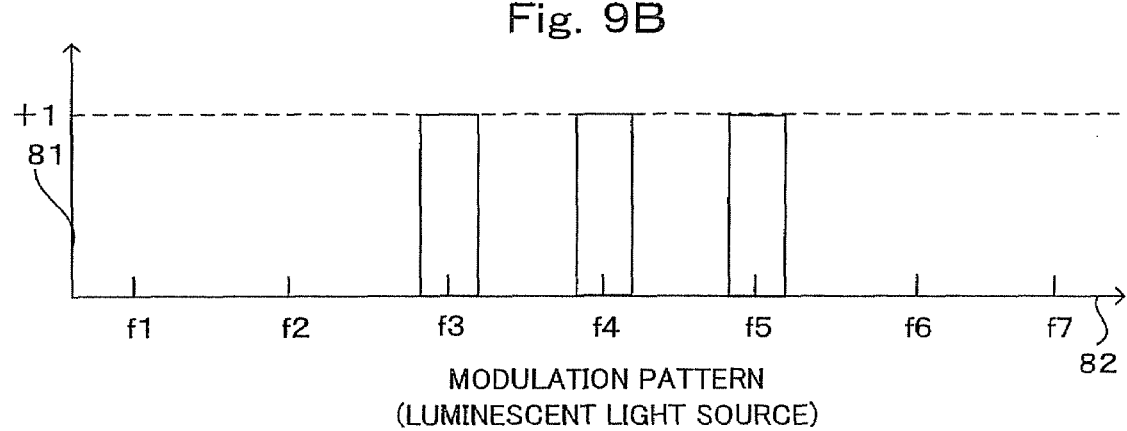
FIG. 9B is a diagram representing an integrated value for each modulation pattern on a record medium having a little gloss on a surface thereof.
Figure 9C:
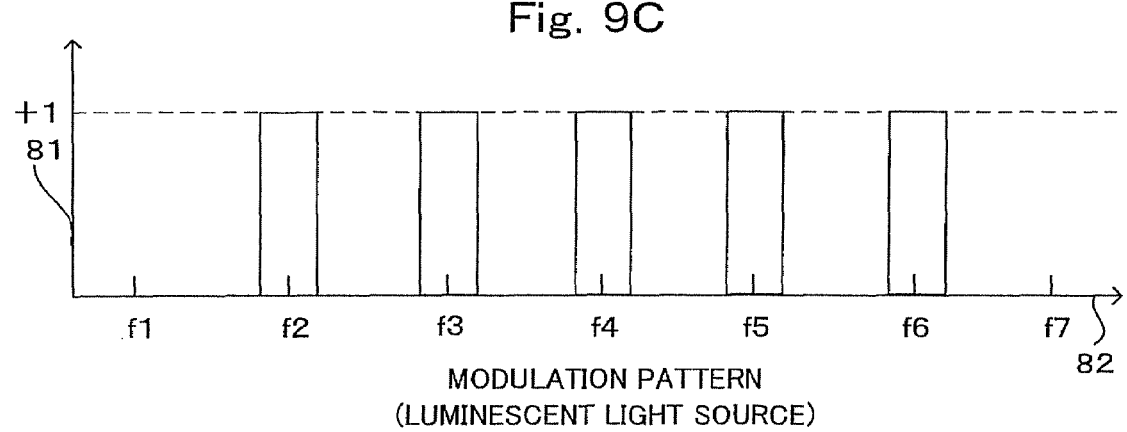
FIG. 9C is a diagram representing an integrated value for each modulation pattern on a record medium having little gloss on a surface thereof.

FIGS. 9A, 9B, and 9C are graphs in which integrated values in the determining device 63 are plotted for each of modulation patterns, i.e., for each of the luminescent light sources 10.

When the record medium 17 is a record medium having a gloss on a surface thereof and reflects light irradiated from the luminescent light sources 10 well, light other than light from f4 among the luminescent light sources 10 is hardly made incident on the photodetector 14. Therefore, as shown in FIG. 9A, an integrated value of a modulation pattern of the light irradiated from f4 is +1 and an integrated value of the other modulation patterns is 0.

When the record medium 17 is a record medium having a little gloss on a surface thereof and reflects light irradiated from the luminescent light sources 10 to some extent, light from f3 and f5 other than f4 among the luminescent light sources 10 is also made incident on the photodetector 14. Therefore, as shown in FIG. 9B, an integrated value of modulation patterns of the light irradiated from f4, f3, and f5 is +1 and an integrated value of the other modulation patterns is 0.

When the record medium 17 is a record medium having little gloss on a surface thereof and does not reflect light irradiated from the luminescent light sources 10 well, light from f2 and f6 in addition to f4, f3, and f5 among the luminescent light sources 10 is also made incident on the photodetector 14. Therefore, as shown in FIG. 9C, an integrated value of modulation patterns of the light irradiated from f4, f3, f5, f2, and f6 is +1 and an integrated value of the other modulation patterns is 0.

As described above, in this applied example, the determining device 63 determines, from integrated values of modulating signals and output signals in the respective modulation patterns, irradiated light from how many luminescent light sources 10 is included in reflected light. The determining device 63 detects glossiness on the surface of the record medium 17 according to whether this number of the luminescent light sources 10 determined is large or small and determines a type of the record medium according to the glossiness.

The determining device 63 determines that the record medium is, for example, an OHP film when the number of frequencies detected is one, high-quality plain paper when the number of frequencies detected is three, and plain paper when the number of frequencies detected is five.

It is possible to set the record-medium determining apparatus 1 according to this embodiment in an image forming apparatus. When the record-medium determining apparatus 1 is set in the image forming apparatus, it is possible to constitute the record-medium determining apparatus 1, for example, as described below. It is suitable to set the record-medium determining apparatus 1 in a position where it is possible to irradiate light from the luminescent light sources 10 on the record medium 17 and light other than the light from the luminescent light sources 10 is made incident a little. A determination result of the record medium by the record-medium determining apparatus 1 is outputted to a control unit of the image forming apparatus. The control unit of the image forming apparatus adjusts a printing method in accordance with this determination result. The control unit of the image forming apparatus is constituted to control operations of the record-medium determining apparatus 1.

As described above, in this embodiment, the plural luminescent light sources 10 are provided in the record-medium determining apparatus 1 and different modulations are given to each of the luminescent light sources 10. The record-medium determining apparatus 1 extracts a signal synchronizing with a modulating signal for giving this modulation from reflected light of the record medium 17, detects the luminescent light sources 10 that have emitted irradiated light included in the reflected light, and determines a type of the record medium. Therefore, there is an effect that it is possible to perform determination of the record medium 17 even if light other than light of the luminescent light sources 10 is present, which is convenient for an operator because it is unnecessary to perform calibration.

Second Embodiment

A schematic structure of a record-medium determining apparatus according to a second embodiment will be explained. This embodiment is characterized in that a set of luminescent light sources are provided in the record-medium determining apparatus, the luminescent light sources irradiate light to move a light and shade pattern in a fixed direction, irradiated light irradiated from the luminescent light source and reflected on a record medium is made incident on a photodetector through a through hole and converted into an electric signal, and a type of the record medium is determined by detecting amplitude of intensity of the signal.

Figure 10:
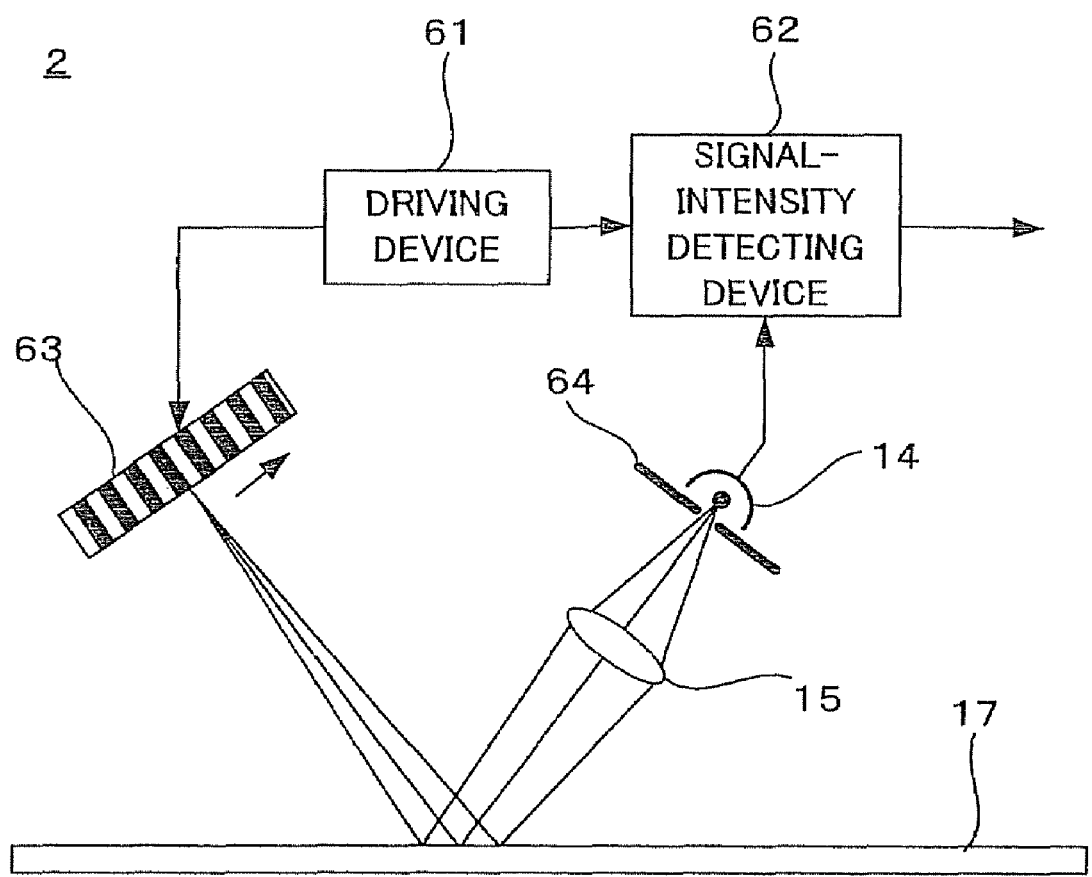
FIG. 10 is a diagram schematically showing a record-medium determining apparatus according to a second embodiment.

FIG. 10 is a diagram schematically showing the record-medium determining apparatus according to this embodiment. A record-medium determining apparatus 2 according to this embodiment includes a set of luminescent light sources 63 that irradiate light to a surface of a record medium, a driving device 61 that controls a pattern of light and shade irradiated from the luminescent light sources 63, a light shielding plate 64 that has a through hole, the photodetector 14 that detects irradiated light reflected on the surface of the record medium 17, and a signal-intensity detecting device 62 that detects a type of the record medium 17 by detecting amplitude of intensity of reflected light from an output signal outputted by converting light detected by the photodetector 14.

A device that can irradiate light to move a light and shade pattern in a fixed direction is used as the luminescent light sources 63. For example, it is possible to use a liquid crystal display, a CRT, or a light source in which a large number of fine LEDs are arranged in a plane shape.

The light shielding plate 64 has a through hole provided such that, when the record medium 17 totally reflects light, reflected light of the irradiated light irradiated from a specific portion of the luminescent light sources 63 is made incident on the photodetector 14 and other reflected lights are not made incident on the photodetector 14.

"The other reflected lights are not made incident" does not means that the other reflected lights are not made incident at all and does not require that the other reflected lights are not made incident at all. It is inevitable that the other reflected lights are slightly made incident. Even in this case, according to this embodiment, it is possible to determine a type of the record medium 17.

The specific portion of the luminescent light sources 63 indicates a part of a light-emitting section of the luminescent light sources 63. For example, it is possible to cite a circle having the center around the center of the luminescent light sources 63 and having a diameter shorter than ½ of a cycle of a spatial frequency of a finest light and shade pattern, i.e., the width of one stripe of a striped pattern of light and shade. In this way, in accordance with a pattern of light and shade irradiated from the luminescent light sources 63, the through hole is provided such that reflected light is made incident on the photodetector 14 at a fixed time interval.

The through hole is a fractured section that is provided in the light shielding plate 64 and causes light to pass. This through hole may be a mere hole or may be formed of a transparent material such as glass. A shape of the through hole is not limited to a circle.

The photodetector 14 only has to have a function of converting light into an electric signal. It is possible to select a type of the photodetector 14 as appropriate. The photodetector may be constituted to condense light with the lenses 15.

Figure 11:
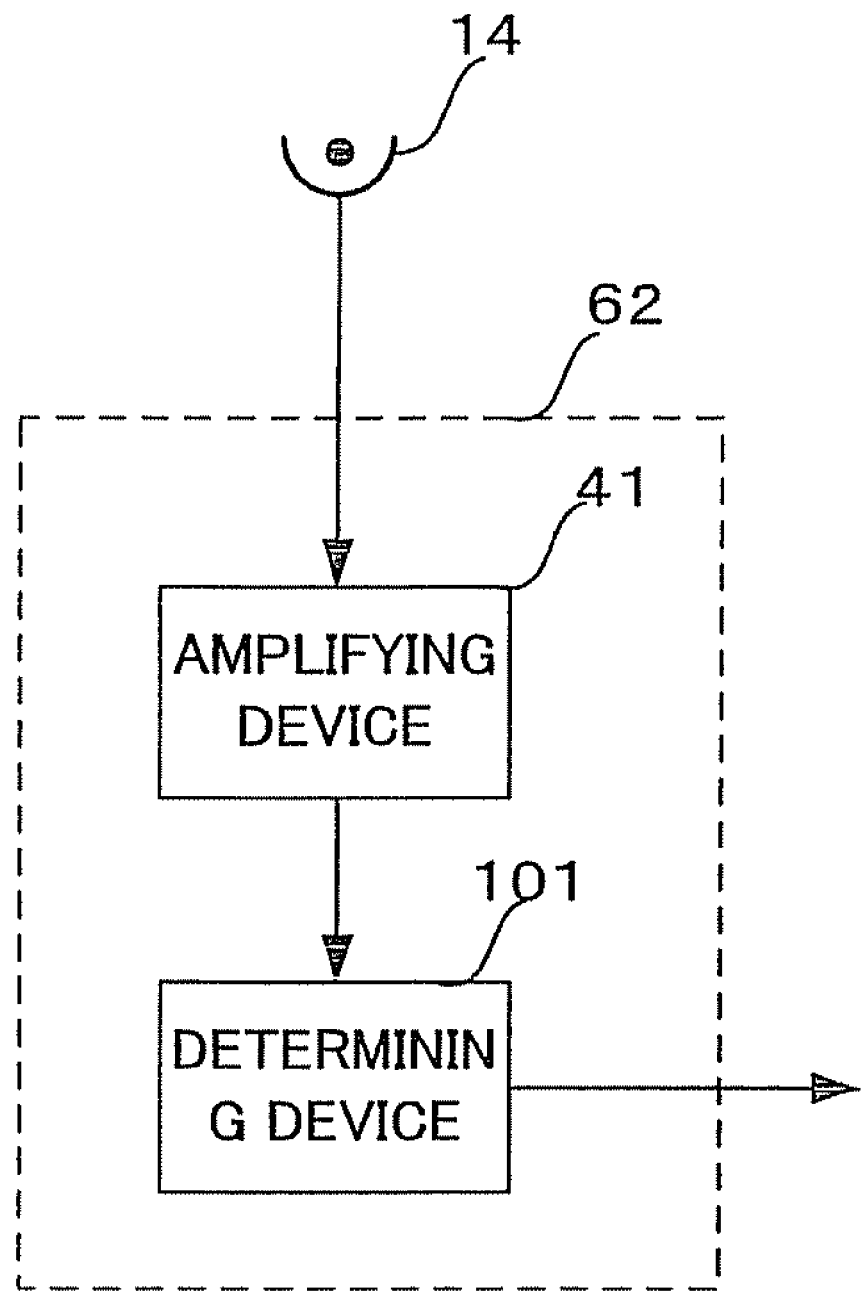
FIG. 11 is a schematic diagram showing a structure and a connection relation of a signal-intensity detecting device according to the second embodiment.

FIG. 11 is a schematic diagram showing a structure and a connection relation of the signal-intensity detecting device 62. Irradiated light reflected on the medium 17 is detected and converted into an electric signal by the photodetector 14. This converted output signal is inputted to the signal-intensity detecting device 62. A modulating signal of the driving device 61 is outputted to the luminescent light sources 63 and the signal-intensity detecting device 62.

The signal-intensity detecting device 62 includes the amplifying device 41 that amplifies an output signal and a determining device 101 that detects contrast of light and shade of reflected light, i.e., amplitude of intensity of the output signal from the output signal, and determines a type of the record medium 17 from this amplitude.

It is possible to constitute the determining device 101, for example, as described below. The determining device 101 includes an A/D converter that changes analog data to digital data, a processor such as a digital signal processor, and a memory that stores data. Moreover, the determining device 101 is inputted with digital data from the A/D converter, compares amplitudes of intensity of output signals at respective modulation frequencies, and stores a program describing processing for determining glossiness of the record medium 17 in the memory. The processor reads the program from this memory and executes the processing.

It is possible to provide this determining device 101 on the outside of the signal-intensity detecting device 62, for example, integrally with a control unit of the image forming apparatus.

(Third Applied Example)

An example in which one kind of a pattern of light and shade irradiated from the luminescent light sources 63 is used will be explained as a third applied example.

Figure 12:
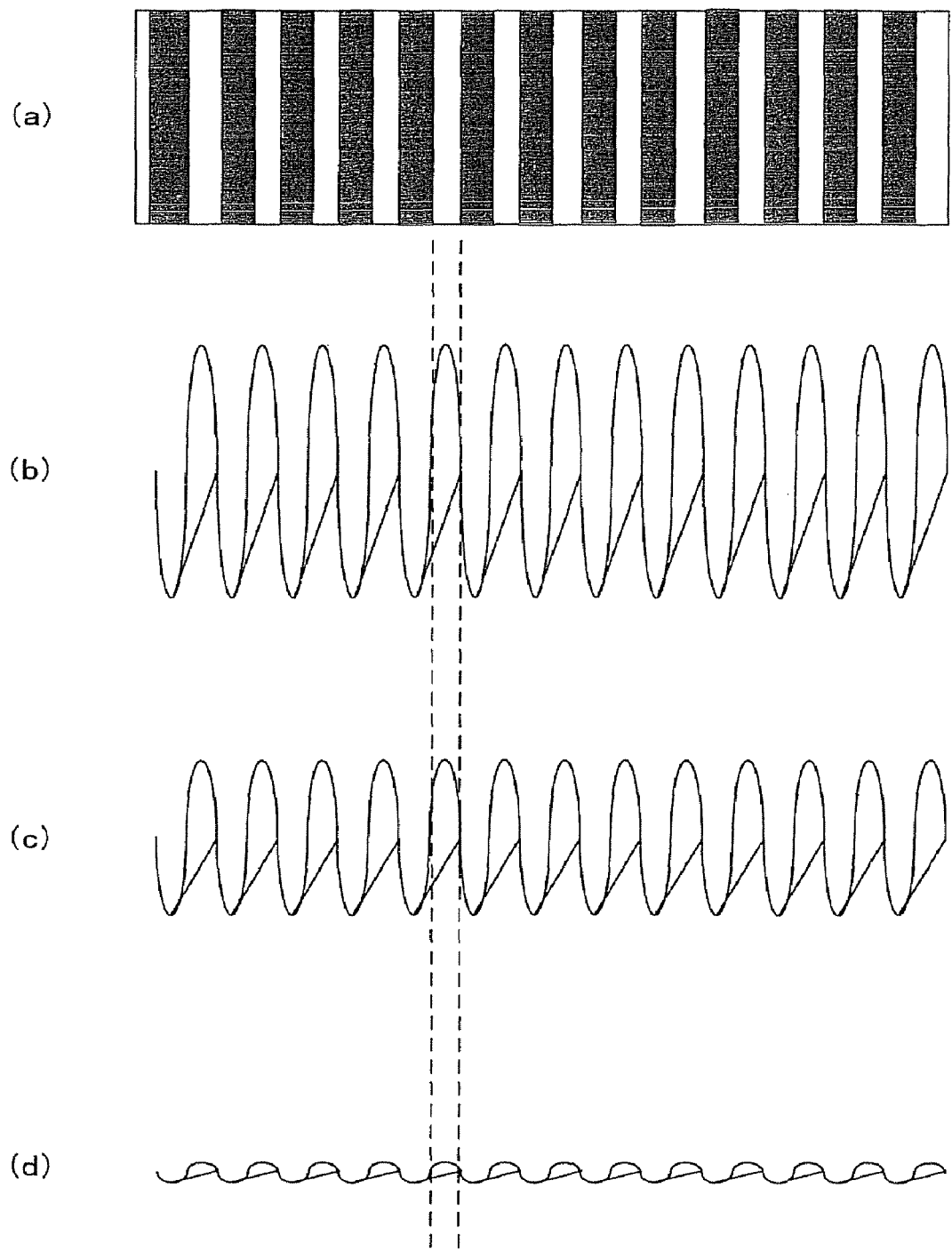
FIG. 12 is a diagram showing reflected light detected as a light and shade pattern.

FIG. 12 is a diagram showing a light and shade pattern and reflected light detected. FIG. 12(a) is a diagram showing an example of a light and shade pattern irradiated from the luminescent light source 63. White portions indicate portions on which light is irradiated and black portions indicate portions on which light is not irradiated. In this example, light is irradiated such that the pattern moves in the horizontal direction.

FIG. 12(b) is a diagram representing amplitude of intensity detected by the determining device 101 from irradiated light from the luminescent light sources 63 reflected on the record medium 17 having a gloss on the surface. As shown in the figure, in the case of the record medium 17 having a gloss, since a pattern of light and shade, i.e., a striped pattern of light and shade is clearly reflected, amplitude is large.

FIG. 12(c) is a diagram representing amplitude of intensity detected by the determining device 101 from irradiated light from the luminescent light sources 63 reflected on the record medium 17 having a slight gloss on the surface. As shown in the figure, in the case of the record medium 17 having a slight gloss, since light slightly scatters on the surface of the record medium 17, a pattern of light and shade is reflected to be slightly blurred. Thus, the amplitude is slightly small.

FIG. 12(d) is a diagram representing amplitude of intensity detected by the determining device 101 from irradiated light from the luminescent light sources 63 reflected on the record medium 17 having a little gloss on the surface. As shown in the figure, in the case of the record medium 17 having a little gloss, since light scatters on the surface of the record medium 17, a pattern of light and shade is reflected to be considerably blurred. Thus, the amplitude is extremely small.

Figure 14:
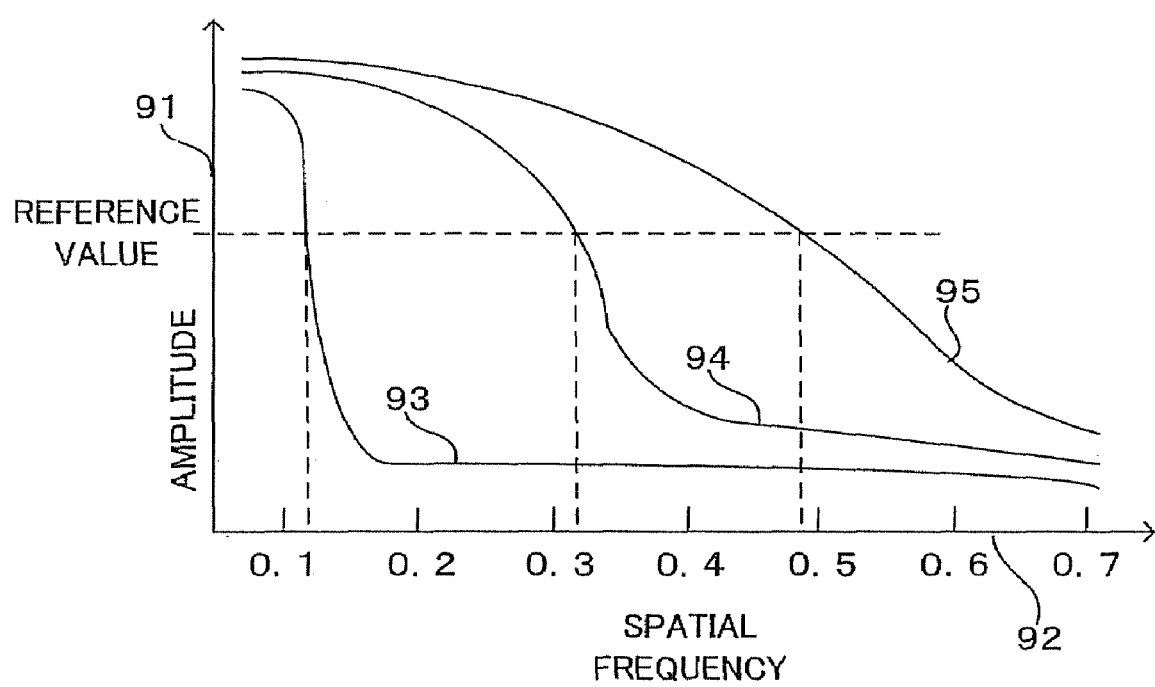
FIG. 14 is a graph in which an average of detected amplitudes is plotted.

As described above, in this applied example, the determining device 101 represents glossiness of the record medium 17 as amplitude of intensity of reflected light and determines a type of a record medium using this amplitude. For example, as shown in FIG. 14, the determining device 101 determines that, when a blinking pattern with a spatial frequency of 0.4 is irradiated, the record medium 17 on which amplitude indicated by a graph 95 is detected is glossy paper because the amplitude exceeds a reference value and the record medium 17 on which amplitude indicated by a graph 94 is detected in plain paper because the amplitude is lower than the reference value.

(Fourth Applied Example)

An example in which plural kinds of patterns of light and shade irradiated from the luminescent light sources 63 are used will be explained as a fourth applied example.

In this applied example, the driving device 61 sequentially changes a spatial frequency of light and shade, the luminescent light sources 63 sequentially irradiate irradiated light having patterns of light and shade with the spatial frequencies changed on the record medium 17, and the signal-intensity detecting device 62 sequentially detects amplitude of intensity of reflected light for each of the spatial frequencies using the method described above.

Figure 13A:
FIG. 13A is a diagram showing an example of a pattern of light and shade of a high spatial frequency.
Figure 13B:
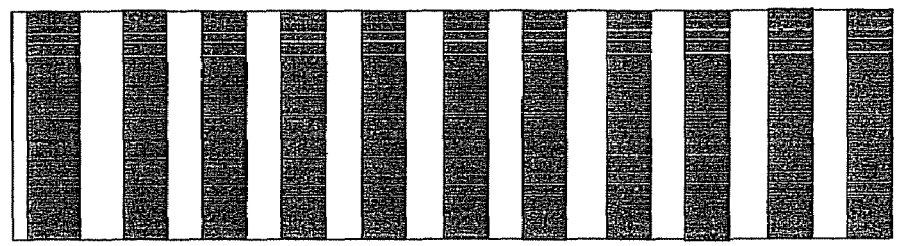
FIG. 13B is a diagram showing an example of a pattern of light and shade of a slightly high spatial frequency.
Figure 13C:
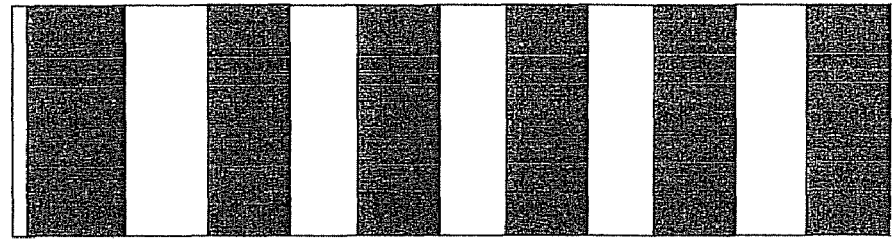
FIG. 13C is a diagram showing an example of a pattern of light and shade of a low spatial frequency.

FIGS. 13A, 13B, and 13C are diagrams showing examples of patterns of light and shade at different spatial frequencies. These patterns of light and shade are irradiated to move in the same direction at the same speed. The spatial frequencies of light and shade are high in FIG. 13A, slightly high in FIG. 13B, and low in FIG. 13C. The spatial frequency means an inverse of a cycle of light and shade. The spatial frequency may change according to discrete values or may change continuously.

FIG. 14 is a graph in which an average of amplitudes detected is plotted. An ordinate 91 indicates an average of amplitudes and an abscissa 92 indicates a spatial frequency of light and shade.

When the record medium 17 is a record medium having a gloss on a surface thereof and reflects light irradiated from the luminescent light sources 10 well, even if the spatial frequency of light and shade is high, a pattern of light and shade, i.e., a striped pattern of light and shade is reflected clearly. Thus, as indicated by a graph 95, even if the spatial frequency is high, the average of amplitudes is large.

When the record medium 17 is a record medium having a little gloss on a surface thereof and reflects light irradiated from the luminescent light sources 10 to some extent, a pattern of light and shade is reflected to be lightly blurred. Therefore, when the spatial frequency of light and shade is high, as indicated by a graph 94, the average of amplitudes is small. However, when the spatial frequency of light and shade is low, the average of amplitudes is large.

When the record medium 17 is a record medium having little gloss on a surface thereof and does not reflect light irradiated from the luminescent light sources 10 well, a pattern of light and shade is reflected to be considerably blurred. Therefore, as indicated by a graph 93, the average of amplitudes is large only when the spatial frequency of light and shade is low.

As described above, in this applied example, the determining device 101 represents glossiness of the record medium 17 using a maximum value of a spatial frequency of light and shade, amplitude of intensity of which takes a value larger than a value set in advance, and determines a type of a record medium using this maximum value of the spatial frequency of light and shade.

For example, as shown in FIG. 14, the determining device 101 determines that the record medium 17 on which a maximum value of a spatial frequency exceeding the reference value exceeds 0.4 is glossy paper. As a result, the record medium 17 on which the amplitude indicated by the graph 95 is detected is determined as glossy paper.

The determining device 101 determines the record medium 17 on which a maximum of a spatial frequency exceeding the reference value exceeds 0.3 and is lower than 0.4 is high-quality plain paper. As a result, the record medium 17 on which the amplitude indicated by the graph 94 is detected is determined as high-quality plain paper.

Moreover, the determining device 101 determines that the record medium 17 on which a maximum value of a spatial frequency exceeding the reference value exceeds 0.1 and is lower than 0.3 is recycled plain paper. As a result, the record medium 17 on which the amplitude indicated by the graph 93 is detected is determined as recycled plain paper.

It is possible to set the record-medium determining apparatus 2 according to this embodiment in an image forming apparatus. When the record-medium determining apparatus is set in the image forming apparatus, it is possible to constitute the record-medium determining apparatus 2, for example, as described below. It is suitable to set the record-medium determining apparatus 2 in a position where it is possible to irradiate light from the luminescent light sources 10 on the record medium 17 and light other than the light from the luminescent light sources 10 is made incident a little. A determination result of the record medium by the record-medium determining apparatus 2 is outputted to a control unit of the image forming apparatus. The control unit of the image forming apparatus adjusts a printing method in accordance with this determination result. The control unit of the image forming apparatus is constituted to control operations of the record-medium determining apparatus 2.

As described above, in this embodiment, the set of luminescent light sources 63 are provided in the record-medium determining apparatus 2 and the luminescent light sources 63 irradiate light to move a pattern of light and shade in a fixed direction. The record-medium determining apparatus 2 detects amplitude of intensity of light of a pattern of light and shade from irradiated light irradiated from the luminescent light sources 63 and reflected on the record medium 17 and determines a type of the record medium 17 using this amplitude.

Therefore, there is an effect that it is possible to reduce the number of components of the luminescent light sources 63 and the signal-intensity detecting device 62 and hold down manufacturing cost. Further, since plural kinds of patterns of light and shade are used, there is an effect that it is possible to improve accuracy of determination of a type of the record medium 17.

<Image Forming Apparatus>

An image forming apparatus will be explained.

Figure 15:
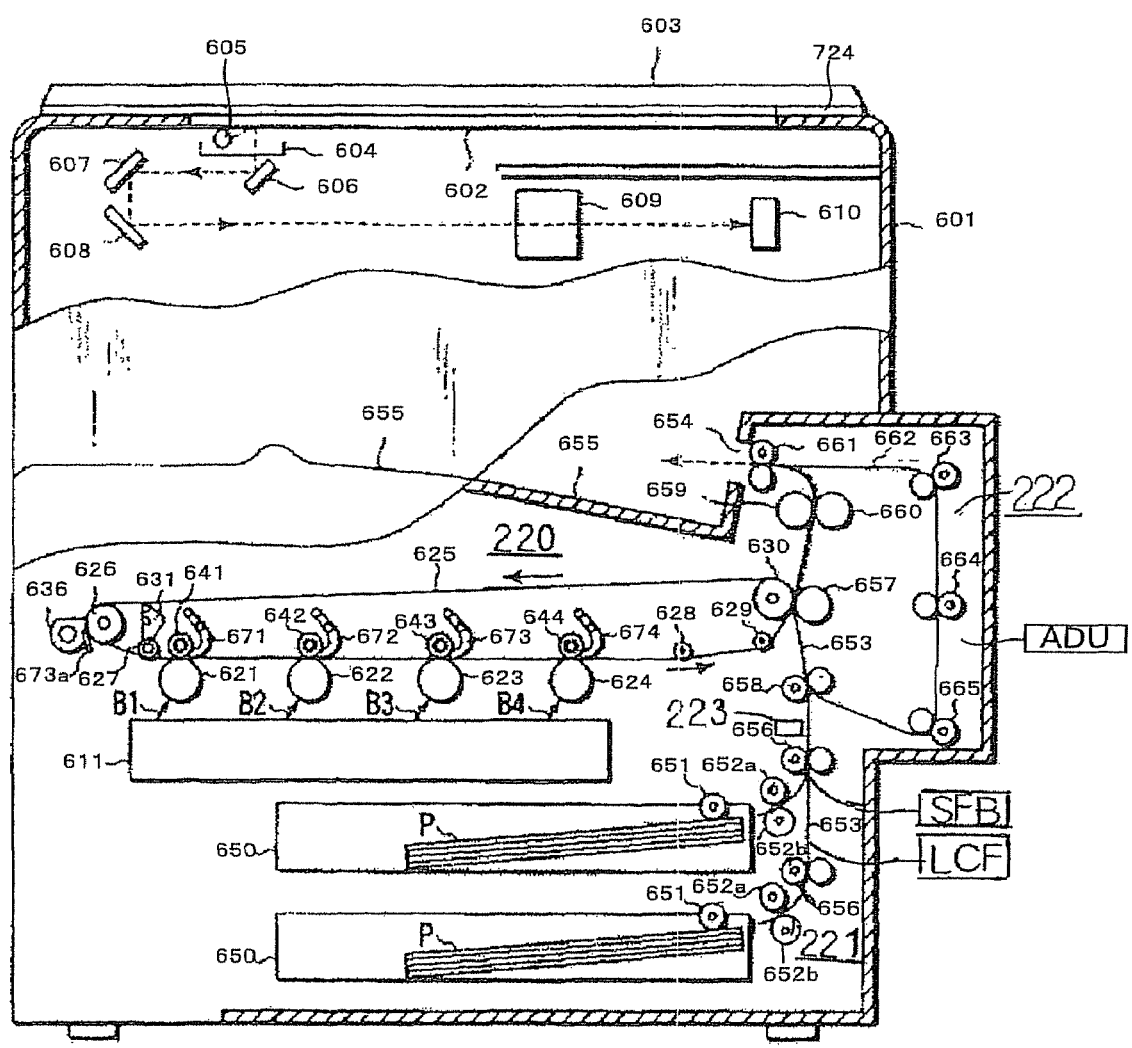
FIG. 15 is a diagram showing an example of a structure of an image forming apparatus.

FIG. 15 is a diagram showing an example of a structure of the image forming apparatus. As shown in FIG. 15, an original stand 602 for original placement formed of a transparent material such as a glass plate is provided in an upper part of an apparatus main body 601. A cover 603 is set in the apparatus main body 601 to be freely opened and closed to cover this original stand 602.

A scan unit (not shown) that optically scans an image of an original placed on the original stand 602 is provided on a lower surface side of the original stand 602 in the apparatus main body 601. For example, this scan unit has a carriage 604, reflecting mirrors 606, 607, and 608 that reflect light of an exposure lamp 605 reflected on the original, a lens block for magnification 609 that changes a magnification of this reflected light, and a CCD (Charge Coupled Device) 610. The carriage 604 includes the exposure lamp 605 that irradiates light to the original stand 602 and is constituted to be reciprocatingly movable along the lower surface of the original stand 602.

The carriage 604 exposes the original placed on the original stand 602 to light by reciprocatingly moving while lighting the exposure lamp 605. A reflected light image of the original placed on the original stand 602 obtained by this exposure is projected on the CCD 610 through the reflecting mirrors 606, 607, and 608 and the lens block for magnification 609. The CCD 610 outputs an image signal corresponding to the reflected light image of the original projected.

An image forming unit 220 is provided below the scan unit in the apparatus main body 601. The image forming unit 220 includes, for example, a print engine (not shown) and a process unit (not shown).

The print engine includes an exposure unit 611. The process unit includes photoconductive drums 621, 622, 623, and 624 arranged along the exposure unit 611, an endless transfer belt 625 arranged to be opposed to the exposure unit 611 across the photoconductive drums 621, 622, 623, and 624, a drive roller 626 that drives the transfer belt 625, primary transfer rollers 641, 642, 643, and 644 arranged to be opposed to the photoconductive drums 621, 622, 623, and 624 across the transfer belt 625, and a transfer-roller driving unit that drives the primary transfer rollers 641, 642, 643, and 644.

The transfer belt 625 is laid over the drive roller 626, guide rollers 627, 628, and 629, and a driven roller 630 and receives power from the drive roller 626 to rotate and travel in a counterclockwise direction. The guide roller 627 is provided to freely move up and down and receives rotation of a cam 631 to move to the transfer belt 625 side. Consequently, the guide roller 627 displaces the transfer belt 625 to the side of the photoconductive drums 621, 622, 623, and 624.

This image forming unit 220 executes an image forming process for forming an image based on image data (an image signal outputted from the CCD 610) and printing the image on a record medium being conveyed. The image signal outputted from the CCD 610 is supplied to the exposure unit 611 after being appropriately processed. The exposure unit 611 emits a laser beam B1 corresponding to an image signal of a yellow color to the photoconductive drum 621 for the yellow color, emits a laser beam B2 corresponding to an image signal of a magenta color to the photoconductive drum 622 for the magenta color, emits a laser beam B3 corresponding to an image signal of a cyan color to the photoconductive drum 623 for the cyan color, and emits a laser beam B4 corresponding to an image signal of a black color to the photoconductive drum 624 for the black color.

The primary transfer rollers 641, 642, 643, and 644 are moved (lowered) to the transfer belt 625 side to bring the transfer belt 625 into contact with the photoconductive drums 621, 622, 623, and 624 and transfer visible images on the photoconductive drums 621, 622, 623, and 624 onto the transfer belt 625.

A drum cleaner, a charge removing lamp, a charging unit, and a developing unit, which are not shown in the figure, are disposed in order around the photoconductive drum 621. The drum cleaner has a drum cleaning blade set in contact with the surface of the photoconductive drum 621 and scrapes off a developing material remaining on the surface of the photoconductive drum 621 with the drum cleaning blade.

The charge removing lamp removes charges remaining on the surface of the photoconductive drum 621. The charging unit charges the surface of the photoconductive drum 621 with electrostatic charges by applying a high voltage to the photoconductive drum 621. The laser beam B1 emitted from the exposure unit 611 is irradiated on the surface of the photoconductive drum 621 subjected to this charging. According to this irradiation, an electrostatic latent image is formed on the surface of the photoconductive drum 621. The developing unit visualizes the electrostatic latent image on the surface of the photoconductive drum 621 by supplying a developing material (a toner) of the yellow color to the surface of the photoconductive drum 621.

In the other photoconductive drums 622, 623, and 624, electrostatic latent images on the surfaces of the respective photoconductive drums 622, 623, and 624 are visualized using developing materials of colors corresponding thereto, respectively, in the same manner.

A cleaner 636 is provided across the transfer belt 625 in a position of the image forming unit 220 opposed to the drive roller 626. This cleaner 636 has a cleaning blade 636a set in contact with the transfer belt 625 and scrapes off a developing material remaining on the transfer belt 625 with the cleaning blade 636a.

Printing modes are changed as follows. Hooks 671, 672, 673, and 674 are provided near the primary transfer rollers 641, 642, 643, and 644. The hooks 671, 672, 673, and 674 engage with shafts of the primary transfer rollers 641, 642, 643, and 644 to lift the shafts while rotating and moves the primary transfer rollers 641, 642, 643, and 644 in a direction apart from the photoconductive drums 621, 622, 623, and 624. Printing modes such as a full color mode, a full separation mode, and a monochrome mode are changed by not moving all the primary transfer rollers 641, 642, 643, and 644 or changing a combination of the primary transfer rollers to be moved.

A storing mechanism and a supplying mechanism for record media will be explained. Plural record medium cassettes 650 that store record media are provided below the exposure unit 611. In these record medium cassettes 650, a large number of record media P of record medium types different from one another are stored in a stacked state. Record-medium supplying mechanisms 221 that supply the record media in the record media cassettes 650 one by one from the top thereof are provided in exit sections (on the right side in the figure) of these record medium cassettes 650, respectively. The record media P are taken out one by one from any one of the record medium cassettes 650 by this record-medium supplying mechanism 221. This record-medium supplying mechanism 221 for taking out the record media includes a pickup roller 651, a record-medium supplying roller 652a, and a separating roller 652b and separates the record media P taken out from the record medium cassette 650 one by one and supplies the record media P to a record-medium conveying path 653.

A conveying path for record media will be explained. The record-medium conveying path 653 extends to a record-medium discharge port 654 in an upper part through the driven roller 630 of the image forming unit 220. The record-medium discharge port 654 faces a record-medium discharging unit 655 extending to an outer peripheral surface of the apparatus main body 601. Conveying rollers 656 are provided near the record-medium supplying mechanisms 221, respectively, on the starting end side of the conveying path 653. When record media are supplied to this record-medium conveying path 653 by any one of the record-medium supplying mechanisms 221, this record-medium conveying path 653 conveys the supplied record medium to the record-medium discharging unit 655.

A secondary transfer roller 657 is provided in a position opposed to the driven roller 630 across the transfer belt 625 along the record-medium conveying path 653. Registration rollers 658 are provided in a position just before the driven roller 630 and the secondary transfer roller 657 in the conveying direction.

The registration rollers 658 feed the record medium P to a space between the transfer belt 625 and the secondary transfer roller 657 at timing synchronizing with a transfer operation, which is an operation for transferring an image formed by a developing material (a toner) onto a record medium, by the transfer belt 625 and the secondary transfer roller 657. The secondary transfer roller 657 transfers, while nipping the record medium P fed from the registration rollers 658 between the secondary transfer roller 657 and the transfer belt 625 on the driven roller 630, a visible image formed by the developing material (the toner) transferred on the transfer belt 625 to this record medium P and prints the visible image. In this way, the registration rollers 658 convey the record medium P to the image forming unit 220 having the transfer belt 625 and the secondary transfer roller 657 in synchronization with the transfer operation of the image forming unit 220.

A heat roller 659 for heat fixing and a press contact roller 660 set in contact with this heat roller 659 are provided in a position further on a downstream side than the second transfer roller 657 of the record-medium conveying path 653. The image transferred on the record medium P is fixed by the heat roller 659 and the press contact roller 660. A record-medium discharge roller 661 is provided at the end of the record-medium conveying path 653.

An automatic duplex unit (hereinafter referred to as ADU) 222 may be provided in the apparatus main body 601. The ADU 222 is set to couple a sub-conveying path 662, which is a path for conveying the record medium P in the ADU 222, to the end of the record-medium conveying path 653 and an entrance to the registration rollers 658. The sub-conveying path 662 branches from a downstream side with respect to the image forming unit 220 of the record-medium conveying path 653 (the end of the record-medium conveying path 653) and joins an upstream side with respect to the image forming unit 220 of this record-medium conveying path 653 (an upstream side position of the registration rollers 658).

This sub-conveying path 662 reverses the front and the rear of the record medium P for duplex printing. Record-medium supplying rollers 663, 664, and 665 are provided in the sub-conveying path 662. The ADU 222 feeds backward the record medium P conveyed from the image forming unit 220 to the record-medium discharging unit 655, conveys the record medium P through the sub-conveying path 662, and causes the record medium P to join the record-medium conveying path 653 on the upstream side of the image forming unit 220. When the record medium P is conveyed in this way, the front and the rear of the record medium P are reversed.

After joining the record-medium conveying path 653, the record medium P returned to the upstream side of the image forming unit 220 by the sub-conveying path 662 is fed into a transfer position where transfer belt 625 and the second transfer roller 657 are in contact by the registration rollers 658 in synchronization with the transfer operation of the image forming unit 220. In this way, the visible image on the transfer belt 625 is also transferred onto the rear surface of the record medium P and printed.

When duplex printing is designated by an operation panel 724 provided in the apparatus main body 601 or a computer or the like connected to the apparatus main body 601 through a network, the sub-conveying path 662 of the ADU 222 comes into a state in which the ADU 222 performs the operation for reversing the front and the rear of the record medium P.

Devices additionally provided will be explained. In the example of the apparatus main body 601 shown in FIG. 15, the two record medium cassettes 650 are provided as supply sources of record media. Three or more record medium cassettes 650 may be provided in the apparatus main body 601. Besides, although not shown in the figure, it is also possible to provide a manual-feed record-medium supplying mechanism (hereinafter referred to as SFB) and a large-capacity record medium feeder (hereinafter referred to as LCF), which is a record-medium supplying mechanism that can store several thousands record media in a stacked state. The SFB and the LCF are set in the apparatus main body 601 such that paths for supplying record media stored therein join the record-medium conveying path 653.

Figure 16:
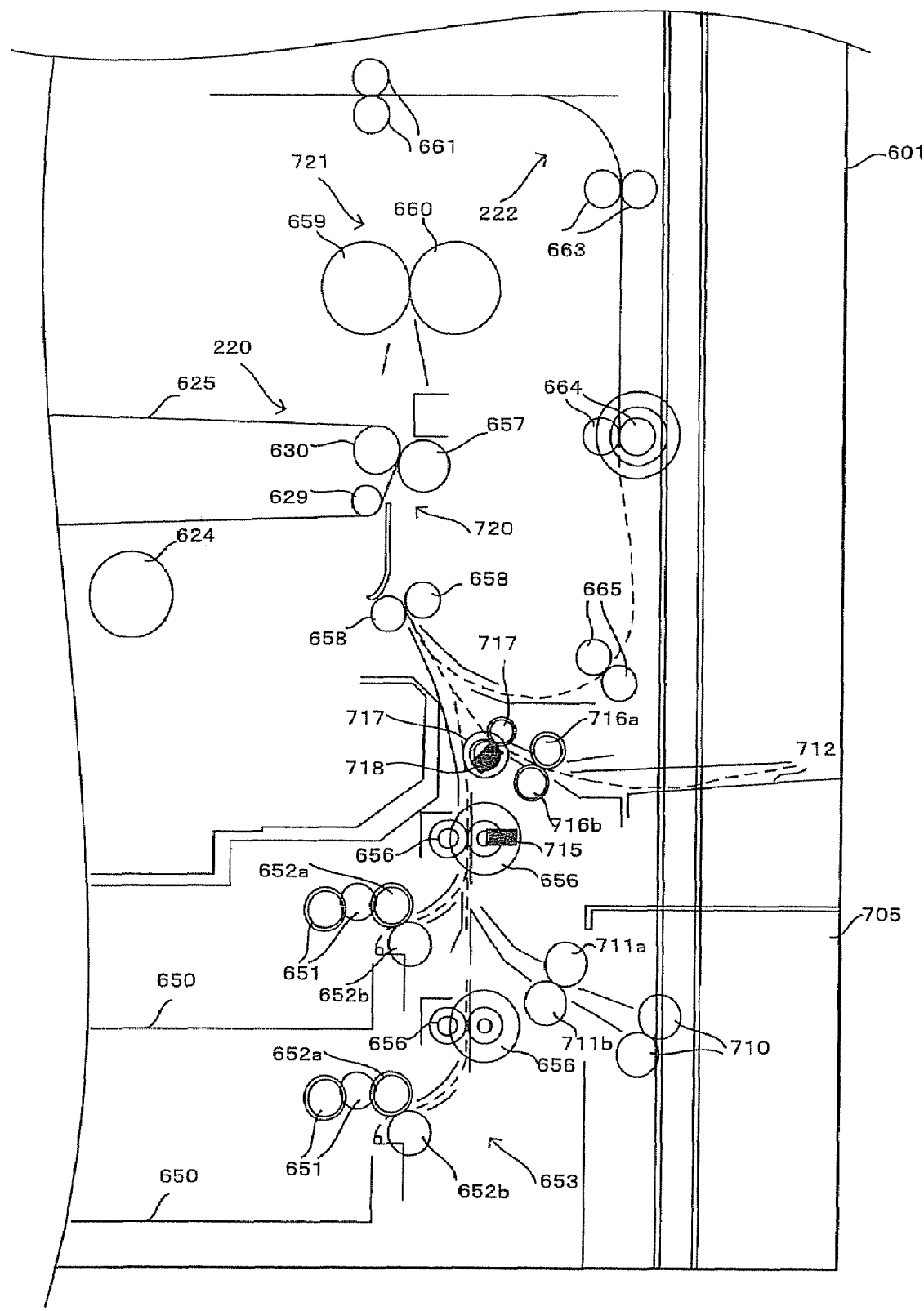
FIG. 16 is a diagram showing a section near a record-medium conveying path in detail.

A setting position of the record-medium determining apparatus 1 or 2 according to this embodiment will be explained. FIG. 16 is a diagram showing a section near the record-medium conveying path 653 in detail. The heat roller 659 and the press contact roller 660 will be hereinafter collectively referred to as a fixing unit 721. When the heat roller 659 heats the record medium P having the developing material (the toner) transferred thereon and the press contact roller 660 conveys the record medium P while applying a pressure thereto, this fixing unit 721 fixes the developing material on the record medium P.

A not-shown control unit is provided in the apparatus main body 601. It is possible to constitute this control unit using, for example, a CPU, memories such as a ROM and a RAM, and an LSI. The control unit controls the temperature of the heat roller 659. For example, when there is no signal from the control unit, the heat roller 659 stays on standby while maintaining a temperature set in advance according to a type of the record medium P. When a signal for starting fixing is received, the heat roller 659 changes the temperature in accordance with an instruction of the signal.

Since the apparatus main body 601 performs the fixing of the developing material by adopting such a constitution, the record-medium determining apparatus 1 or 2 is set further on the upstream side than the fixing unit 721 of the record-medium conveying path 653.

When only one record-medium determining apparatus 1 or 2 is used, the record-medium determining apparatus is set in a first setting position 223 shown in FIG. 15. The first setting position 223 is a position on the upstream side with respect to the image forming unit 220 of the record-medium conveying path 653 and further on the upstream side than the registration rollers 658. When an SFB 712 or an LCF 705 is set, the first setting position 223 is a position further on the downstream side than joining points of record-medium supplying paths from the SFB 712 and the LCF 705 and the record-medium conveying path 653. The record-medium determining apparatus 1 or 2 is set to face a surface of a record medium conveyed.

By arranging the record-medium determining apparatus 1 or 2 in this first setting position 223, it is possible to detect types of the record media P conveyed on the record-medium conveying path 653 from all the supply sources of record media using one record-medium determining apparatus 1 or 2.

Depending on a model of the image forming apparatus, it may be impossible to set the record-medium determining apparatus 1 or 2 in the first setting position 223 because of a relation of arrangement of the various components in the apparatus main body 601. In some models, the SFB 712 is attached as an option. In these cases, it is also possible to provide the record-medium determining apparatus 1 or 2 in the following two positions.

The positions will be explained using FIG. 16. In the record-medium conveying path 653, a second setting position 715 is a position further on the upstream side than the image forming unit 220 of the record-medium conveying path 653 and further on the upstream side than the registration rollers 658 and a position on the downstream side of the record-medium supplying roller 652a and the separating roller 652b of the cassette device 650 at an uppermost stage and further on the downstream side than the joining position of the record-medium supplying path from the LCF 705 and the record-medium conveying path 653. The record-medium determining apparatus 1 or 2 is set to face a surface of a record medium conveyed. The record-medium determining apparatus 1 or 2 may be set near the conveying rollers 656 in the second setting position 715.

A third setting position 718 is a position further on the upstream side than the joining position of the record-medium supplying path from the SFB 712 and the record-medium conveying path 653. The record-medium determining apparatus 1 or 2 is set to face a surface of a record medium conveyed. The record-medium determining apparatus 1 or 2 may be set near conveying rollers 717 in the third setting position 718.

By arranging the record-medium determining apparatus 1 or 2 in the second setting position 715 and the third setting position 718, in a model in which the SFB 712 is attached as an option, there is an effect that it is possible to set the record-medium determining apparatus 1 or 2 in the setting position 718 when necessary.

An applied example concerning processing of a signal of a determination result outputted from the record-medium determining apparatus 1 or 2 will be explained. The operation panel 724 used for selecting a type of the record medium P and used for input in the case of display of information and data setting is attached to an upper surface of the apparatus main body 601. The operation panel 724 is connected to the control unit. This control unit controls speed of a motor that drives to rotate the respective rollers for conveying a record medium and also performs stop and restart of conveyance of the record medium.

First, the control unit stores a default type of a record medium or a type of a record medium inputted through the operation panel 724 in a memory as a setting record medium and sets a standby temperature of the heat roller 659 corresponding to this setting record medium.

When the record medium P is conveyed and the record-medium determining apparatus 1 or 2 determines a type of the record medium P, the record-medium determining apparatus 1 or 2 outputs a signal of a determination result to the control unit. The control unit sets, for example, a conveying speed of a record medium, a rotation speed of the fixing unit 721, and the temperature at the time of fixing of the heat roller 659 in accordance with the determination result and transmits an instruction to these devices.

As described above, the image forming apparatus in this applied example sets the setting record medium first and, then, further sets conditions such as speed and temperature at the time of fixing in accordance with a type of a record medium determined by the record-medium determining apparatus 1 or 2. Therefore, there is an effect that it is possible to quickly perform more detailed condition setting at the time of the fixing and execution of the fixing corresponding to the type of the record medium.

Although exemplary embodiments of the present invention have been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claims is:

1. A record-medium determining apparatus comprising:
plural luminescent light sources that irradiate light of different frequencies to a surface of a record medium;
a photodetector that detects reflected light irradiated from the luminescent light source and reflected by the record medium;
a light shielding plate that has a through hole provided such that, when the irradiated light totally reflects on the surface of the record medium, reflected light of the irradiated light irradiated from a specific luminescent light source among the plural luminescent light sources is made incident on the photodetector and reflected light of the irradiated light irradiated from portions of the other luminescent light sources is not made incident on the photodetector; and
a signal-intensity detecting device that determines a type of the record medium according to whether a number of frequencies that are detected is large or small by detecting intensity of frequencies of each of the incident lights from an output signal of the photodetector by converting the light detected by the photodetector into an electric signal.

2. A record-medium determining apparatus comprising:
plural luminescent light sources that irradiate light to a surface of a record medium;
a driving device that outputs a modulating signal for giving modulations different for each of the plural luminescent light sources to the irradiated light irradiated from the plural luminescent light sources;
a photodetector that detects reflected light irradiated from the luminescent light sources and reflected by the record medium;
a light shielding plate that has a through hole provided such that, when the irradiated light totally reflects on the surface of the record medium, reflected light of the irradiated light irradiated from a specific luminescent light source among the luminescent light sources is made incident on the photodetector and reflected light of the irradiated light irradiated from portions of the other luminescent light sources is not made incident on the photodetector; and
a signal-intensity detecting device that extracts a signal for each of the modulations from an output signal of the photodetector by converting the light detected by the photodetector into an electric signal and determines a type of the record medium according to whether the number of modulated lights that are extracted is large or small.

3. A record-medium determining apparatus comprising:
plural luminescent light sources that irradiate light to a surface of a record medium;
a driving device that gives frequencies different for each of the plural luminescent light sources to the irradiated light irradiated from the plural luminescent light sources;
a photodetector that detects reflected light irradiated from the plural luminescent light sources and reflected by the record medium;
a light shielding plate that has a through hole provided such that, when the irradiated light totally reflects on the surface of the record medium, reflected light of the irradiated light irradiated from a specific luminescent light source among the luminescent light sources is made incident on the photodetector and reflected light of the irradiated light irradiated from the other luminescent light sources is not made incident on the photodetector; and
a signal-intensity detecting device that detects amplitude for each of the frequencies from an output signal of the photodetector by converting the light detected by the photodetector into an electric signal and determines a type of the record medium according to whether a number of frequencies of each of the incident lights that are extracted is large or small.

4. A record-medium determining apparatus comprising:
plural luminescent light sources that irradiate light to a surface of a record medium;
a driving device that gives blinking patterns different for each of the luminescent light sources to the irradiated light irradiated from the luminescent light sources;
a photodetector that detects reflected light irradiated from the luminescent light sources and reflected by the record medium;
a light shielding plate that has a through hole provided such that, when the irradiated light totally reflects on the surface of the record medium, reflected light of the irradiated light irradiated from a specific luminescent light source among the luminescent light sources is made incident on the photodetector and reflected light of the irradiated light irradiated from the other luminescent light sources is not made incident on the photodetector; and
a signal-intensity detecting device that detects a number of signals for each of the blinking patterns from an output signal outputted by converting the light detected by the photodetector into an electric signal and determines a type of the record medium according to whether the number is large or small.

5. A record-medium determining apparatus comprising:
a luminescent light source that irradiates light to a surface of a record medium to move a light and shade pattern in a fixed direction;
a driving device that gives modulation to a spatial frequency of the light and shade pattern of the irradiated light irradiated from the luminescent light source;
a photodetector that detects reflected light irradiated from the luminescent light source and reflected by the record medium;
a light shielding plate that has a through hole provided such that, when the irradiated light totally reflects on the surface of the record medium, reflected light of the irradiated light irradiated from a specific portion of the luminescent light source is made incident on the photodetector and reflected light of the irradiated light irradiated from other portions of the luminescent light source is not made incident on the photodetector; and a signal-intensity detecting device that determines a type of the record medium by detecting amplitude from an output signal outputted by converting the light detected by the photodetector into an electric signal.

6. A record-medium determining apparatus according to claim 5, wherein the driving device sequentially changes the spatial frequency of the irradiated light temporally, and the signal-intensity detecting device detects amplitude of intensity of reflected light for each spatial frequency from an output signal outputted by converting the reflected light detected by the photodetector and determines a type of the record medium according to a maximum value of a special frequency, amplitude of intensity of the reflected light for which takes a value larger than a value set in advance.

7. An image forming apparatus that forms an image on a record medium, comprising:

a record-medium supplying mechanism that supplies record media one by one;

a record-medium conveying path that conveys the record medium supplied by the record-medium supplying mechanism to a record-medium discharging unit;

an image forming unit configured to be arranged further on an upstream side than the record-medium discharging unit of the record-medium conveying path and execute an image forming process for printing an image based on image data on the record medium conveyed by the record-medium conveying path;

a fixing unit configured to fix a developing material on the record medium with a predetermined temperature;

a record-medium determining apparatus that is provided further on the upstream side of the record-medium conveying path than the fixing unit and detects a type of the record medium; and a control unit configured to change a condition in executing the image forming process according to the type of the record medium determined by the record-medium determining apparatus, the record-medium determining apparatus comprising:

plural luminescent light sources that irradiate light of different frequencies to a surface of the record medium;

a photodetector that detects reflected light irradiated from the luminescent light source and reflected by the record medium;

a light shielding plate that has a through hole provided such that, when the irradiated light totally reflects on the surface of the record medium, reflected light of the irradiated light irradiated from a specific luminescent light source among the plural luminescent light sources is made incident on the photodetector and reflected light of the irradiated light irradiated from portions of the other luminescent light sources is not made incident on the photodetector; and a signal-intensity detecting device that determines a type of the record medium according to whether a number of frequencies that are detected is large or small by detecting intensity of frequencies of each of the incident lights from an output signal of the photodetector by converting the light detected by the photodetector into an electric signal.

8. An image forming apparatus that forms an image on a record medium, comprising:

a record-medium supplying mechanism that supplies record media one by one;

a record-medium conveying path that conveys the record medium supplied by the record-medium supplying mechanism to a record-medium discharging unit;

an image forming unit configured to be arranged further on an upstream side than the record-medium discharging unit of the record-medium conveying path and execute an image forming process for printing an image based on image data on the record medium conveyed by the record-medium conveying path;

a fixing unit configured to fix a developing material on the record medium with a predetermined temperature;

a record-medium determining apparatus that is provided further on the upstream side of the record-medium conveying path than the fixing unit and detects a type of the record medium; and a control unit configured to change a condition in executing the image forming process according to the type of the record medium determined by the record-medium determining apparatus, the record-medium determining apparatus comprising:

plural luminescent light sources that irradiate light to a surface of the record medium;

a driving device that outputs a modulating signal for giving modulations different for each of the plural luminescent light sources to the irradiated light irradiated from the luminescent light sources;

a photodetector that detects reflected light irradiated from the plural luminescent light sources and reflected by the record medium;

a light shielding plate that has a through hole provided such that, when the irradiated light totally reflects on the surface of the record medium, reflected light of the irradiated light irradiated from a specific luminescent light source among the luminescent light sources is made incident on the photodetector and reflected light of the irradiated light irradiated from portions of the other luminescent light sources is not made incident on the photodetector; and a signal-intensity detecting device that extracts a signal for each of the modulations from an output signal of the photodetector by converting the light detected by the photodetector into an electric signal and determines a type of the record medium according to whether a number of modulated lights that are extracted is large or small.

9. An image forming apparatus that forms an image on a record medium, comprising:

a record-medium supplying mechanism that supplies record media one by one;

a record-medium conveying path that conveys the record medium supplied by the record-medium supplying mechanism to a record-medium discharging unit;

an image forming unit configured to be arranged further on an upstream side than the record-medium discharging unit of the record-medium conveying path and execute an image forming process for printing an image based on image data on the record medium conveyed by the record-medium conveying path;

a fixing unit configured to fix a developing material on the record medium with a predetermined temperature;

a record-medium determining apparatus that is provided further on the upstream side of the record-medium conveying path than the fixing unit and detects a type of the record medium; and a control unit configured to change a condition in executing the image forming process according to the type of the record medium determined by the record-medium determining apparatus, the record-medium determining apparatus comprising:

plural luminescent light sources that irradiate light to a surface of the record medium;

a driving device that gives frequencies different for each of the plural luminescent light sources to the irradiated light irradiated from the plural luminescent light sources;

a photodetector that detects reflected light irradiated from the plural luminescent light sources and reflected by the record medium;

a light shielding plate that has a through hole provided such that, when the irradiated light totally reflects on the surface of the record medium, reflected light of the irradiated light irradiated from a specific luminescent light source among the plural luminescent light sources is made incident on the photodetector and reflected light of the irradiated light irradiated from the other luminescent light sources is not made incident on the photodetector; and a signal-intensity detecting device that detects amplitude for each of the frequencies from an output signal of the photodetector by converting the light detected by the photodetector into an electric signal and determines a type of the record medium according to whether a number of modulated lights that are extracted is large or small.

10. An image forming apparatus that forms an image on a record medium, comprising:

a record-medium supplying mechanism that supplies record media one by one;

a record-medium conveying path that conveys the record medium supplied by the record-medium supplying mechanism to a record-medium discharging unit;

an image forming unit configured to be arranged further on an upstream side than the record-medium discharging unit of the record-medium conveying path and execute an image forming process for printing an image based on image data on the record medium conveyed by the record-medium conveying path;

a fixing unit configured to fix a developing material on the record medium with a predetermined temperature;

a record-medium determining apparatus that is provided further on the upstream side of the record-medium conveying path than the fixing unit and detects a type of the record medium; and a control unit configured to change a condition in executing the image forming process according to the type of the record medium determined by the record-medium determining apparatus, the record-medium determining apparatus comprising:

plural luminescent light sources that irradiate light to a surface of the record medium;

a driving device that gives blinking patterns different for each of the luminescent light sources to the irradiated light irradiated from the luminescent light sources;

a photodetector that detects reflected light irradiated from the luminescent light sources and reflected by the record medium;

a light shielding plate that has a through hole provided such that, when the irradiated light totally reflects on the surface of the record medium, reflected light of the irradiated light irradiated from a specific luminescent light source among the luminescent light sources is made incident on the photodetector and reflected light of the irradiated light irradiated from the other luminescent light sources is not made incident on the photodetector; and a signal-intensity detecting device that detects a number of signals for each of the blinking patterns from an output signal outputted by converting the light detected by the photodetector into an electric signal and determines a type of the record medium according to whether the number is large or small.

11. An image forming apparatus that forms an image on a record medium, comprising:

a record-medium supplying mechanism that supplies record media one by one;

a record-medium conveying path that conveys the record medium supplied by the record-medium supplying mechanism to a record-medium discharging unit;

an image forming unit configured to be arranged further on an upstream side than the record-medium discharging unit of the record-medium conveying path and execute an image forming process for printing an image based on image data on the record medium conveyed by the record-medium conveying path;

a fixing unit configured to fix a developing material on the record medium with a predetermined temperature;

a record-medium determining apparatus that is provided further on the upstream side of the record-medium conveying path than the fixing unit and detects a type of the record medium; and a control unit configured to change a condition in executing the image forming process according to the type of the record medium determined by the record-medium determining apparatus, the record-medium determining apparatus comprising:

a luminescent light source that irradiates light to a surface of the record medium to move a light and shade pattern in a fixed direction;

a driving device that gives modulation to a spatial frequency of the light and shade pattern of the irradiated light irradiated from the luminescent light source;

a photodetector that detects reflected light irradiated from the luminescent light source and reflected by the record medium;

a light shielding plate that has a through hole provided such that, when the irradiated light totally reflects on the surface of the record medium, reflected light of the irradiated light irradiated from a specific portion of the luminescent light source is made incident on the photodetector and reflected light of the irradiated light irradiated from other portions of the luminescent light source is not made incident on the photodetector; and a signal-intensity detecting device that determines a type of the record medium by detecting amplitude from an output signal outputted by converting the light detected by the photodetector into an electric signal.

* * * * *